(12) United States Patent
Nam et al.

(10) Patent No.: US 12,050,224 B2
(45) Date of Patent: Jul. 30, 2024

(54) COMPOUNDS USEFUL AS NEAR-INFRARED FLUORESCENT PROBES SELECTIVELY BINDING TO TAU AGGREGATES AND METHOD OF PREPARING THE SAME

(71) Applicant: KOREA INSTITUTE OF SCIENCE AND TECHNOLOGY, Seoul (KR)

(72) Inventors: Ghil Soo Nam, Seoul (KR); Hyun Ah Choo, Seoul (KR); Ahmed A. Elbatrawy, Seoul (KR); Gyo Chang Keum, Seoul (KR); Yun Kyung Kim, Seoul (KR); Sung Su Lim, Seoul (KR); Jae Kyun Lee, Seoul (KR); Eun Kyoung Bang, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 46 days.

(21) Appl. No.: 17/021,438

(22) Filed: Sep. 15, 2020

(65) Prior Publication Data

US 2021/0255203 A1    Aug. 19, 2021

(30) Foreign Application Priority Data

Feb. 12, 2020 (KR) .................. 10-2020-0016824

(51) Int. Cl.
*G01N 33/68* (2006.01)
*C07D 215/20* (2006.01)
*C07D 215/48* (2006.01)
*C07D 401/06* (2006.01)
*G01N 33/58* (2006.01)

(52) U.S. Cl.
CPC ....... *G01N 33/6896* (2013.01); *C07D 215/20* (2013.01); *C07D 215/48* (2013.01); *C07D 401/06* (2013.01); *G01N 33/582* (2013.01); *G01N 2800/2814* (2013.01); *G01N 2800/2821* (2013.01); *G01N 2800/2835* (2013.01)

(58) Field of Classification Search
CPC .................. C07D 215/20; G01N 33/6896
See application file for complete search history.

(56) References Cited

U.S. PATENT DOCUMENTS

| 7,118,730 | B2 | 10/2006 | Kudo et al. | |
| 7,619,091 | B2 | 11/2009 | Barnham et al. | |
| 2010/0279340 | A1 | 11/2010 | Wisniewski et al. | |
| 2015/0239878 | A1* | 8/2015 | Higuchi | C07D 405/06 |
| | | | | 546/171 |
| 2017/0189566 | A1* | 7/2017 | Tu | A61K 51/0465 |

FOREIGN PATENT DOCUMENTS

| CN | 110066243 | A | 7/2019 | |
| EP | 2767532 | A1 * | 8/2014 | ......... A61K 49/0017 |
| KR | 10-2013-0129975 | A | 11/2013 | |
| KR | 10-2015-0095610 | A | 8/2015 | |
| KR | 10-2016-0072226 | A | 6/2016 | |
| KR | 10-1749808 | B1 | 6/2017 | |
| KR | 10-1802672 | B1 | 11/2017 | |
| KR | 10-2018-0052611 | A | 5/2018 | |
| WO | 2013/148228 | A1 | 10/2013 | |
| WO | 2015/060365 | A1 | 4/2015 | |

OTHER PUBLICATIONS

STN registry. American Chemical Society. Chemical Abstract Service. Entered into STN: Aug. 25, 2021 (Year: 2021).*
American Chemical Society. Chemical Abstract Service. RN 130520-71-7. Entered into STN: Nov. 16, 1990 (Year: 1990).*
American Chemical Society. Chemical Abstract Service. RN 130520-68-2, entered Nov. 16, 1990 (Year: 1990).*
Wang et al., "Simple Synthesis of carbon-11 labeled styryl dyes as new potential PET RNA-Specific, living cell imaging probes", European Journal of Medical Chemistry, vol. 44, Mar. 7, 2008, pp. 2300-2306 (Year: 2008).*
ACT on STN (RN No. 130520-71-7, Nov. 16, 1990 and RN No. 130520-68-2, Nov. 16, 1990).
F. C. Mathur et al., Attempts to find New Antimalarials. Part XI . Some Aminoalkylarylquinoline Derivatives., J. Chem. Soc., Jan. 1, 1934, pp. 1520-1523.
K.K. Hsu et al., Synthesis of 2-(6-Methoxy..2-Quinolyl) Chromone Derivatives, J. The Chinese Chem. Soc., 1976, pp. 17-19 , vol. 26, No. 1.
Hualong Fu et.al., Highly Sensitive Near-Infrared Fluorophores for in Vivo Detection of Amyloid-β Plaques in Alzheimer's Disease, J. Med. Chem., Aug. 11, 2015, pp. 6972-6983, vol. 58.

* cited by examiner

*Primary Examiner* — John S Kenyon
*Assistant Examiner* — Gillian A Hutter
(74) *Attorney, Agent, or Firm* — Goldilocks Zone IP Law

(57) ABSTRACT

Disclosed are a compound with near-infrared fluorescence that selectively binds to tau aggregates, a method for preparing the same, a tau-targeting near-infrared fluorescent probe including the compound, a composition for detecting a tau fiber protein containing the near-infrared fluorescent probe as an active ingredient, and the use of the composition for the diagnosis of tauopathy. In particular, the compound does not bind to an amyloid beta protein and has high selectivity to a tau aggregate, specifically reported as an etiology of the initial state of tauopathy, thus being useful as a near-infrared fluorescent detector for detecting a tau fiber protein for early diagnosis of a tauopathy including Alzheimer's disease.

5 Claims, 5 Drawing Sheets

COMPOUNDS USEFUL AS NEAR-INFRARED FLUORESCENT PROBES SELECTIVELY BINDING TO TAU AGGREGATES AND METHOD OF PREPARING THE SAME

CROSS-REFERENCE TO RELATED APPLICATION

This application claims under 35 U.S.C. § 119(a) the benefit of priority to Korean Patent Application No. 10-2020-0016824 filed on Feb. 12, 2020, the entire contents of which are incorporated herein by reference.

BACKGROUND

(a) Technical Field

The present invention relates to a compound having high selectivity for a tau aggregate, a method for preparing the same, a tau-targeting near-infrared fluorescent probe including the compound, a composition for detecting a tau fiber protein containing the near-infrared fluorescent probe as an active ingredient, and the use of the composition for diagnosis of a tauopathy.

(b) Background Art

As the population is aging, degenerative dementia, which is a degenerative neurological disease commonly observed in older people, has emerged as a serious issue.

Meanwhile, medical imaging tests make an important contribution to the diagnosis and treatment of patients. The recent introduction of reporter gene technology has drawn a great deal of attention to molecular imaging, capable of imaging changes at the molecular level and cell level in vivo. Molecular imaging is a non-invasive method of imaging life phenomena in cells or molecular units of living organisms, and can help diagnose diseases by imaging minute functional differences in the initial state, before onset of anatomical changes caused by diseases. Therefore, molecular imaging detects and treats conditions before diseases in an early stage, presents new possibilities in the development of therapeutic drugs, and enables early evaluation of post-treatment responses, thus minimizing toxicity associated with treatment and providing treatment suitable for respective patients. Inspection methods for obtaining such images include single photon emission computed tomography (SPECT) and positron emission tomography (PET) using radioactive elements. Molecular imaging using nuclear medicine techniques such as SPECT and PET has been developed very rapidly to evaluate the function of the central nervous system, and is a useful practical technique in basic medical research and clinical practice. In particular, research is being actively conducted to develop a radioactive probe for PET to image the accumulation of agents causative of Alzheimer's disease. To date, beta-amyloid is known as the main etiology of Alzheimer's disease, and diagnosis of Alzheimer's disease is also performed through positron emission tomography (PET) using a labeling compound that binds to beta-amyloid. However, PET imaging using a beta-amyloid probe is of limited usefulness in the early diagnosis of patients with dementia because beta-amyloid is observed in normal people and is known to have a very low correlation with Alzheimer's-related dementia, thus being of. In addition, since the positron tomography method uses a probe labeled with a radioisotope, it is limited as a biological imaging method because production and use thereof are possible only in special facilities, and entails drawbacks of requiring special equipment and incurring high costs.

Meanwhile, a tau protein has the function of stabilizing the tubulin structure, which constitutes the brain's nervous system. A tau protein is composed of 352 to 441 amino acids and has six isoforms depending on the composition. Tau441 (2N4R), the longest form, accounts for more than 85% thereof and undergoes phosphorylation in serine, threonine and tyrosine, and an overphosphorylated tau form thereof is known to be present in patients with brain diseases such as Alzheimer's disease. As a result, it has been reported that the relationship with the disease is close, and compounds developed as targets can be used as main biomarkers. Tau proteins are positively charged and thus neutralized in water-soluble or hyperphosphorylated forms, and are not well attached to microtubules and are easily detached therefrom. The tau single molecules resulting from such detachment are known to form paired helical filaments (PHFs) and to be entangled with one another and be present as "Tau neurofibril tangles (NFTs)". Therefore, the degree of disease progression can be predicted from the concentration of the amount of tau present by type. To date, entanglement of a large amount of amyloid beta protein has been found in the brain of patients with dementia, including Alzheimer's disease, and the presence or absence of amyloid beta protein is an important disease biomarker. However, an amyloid beta protein has been found to be present in a considerable amount in the brain of normal people, and is of limited use in diagnosing the disease because there is no difference in disease progression from the initial state to a severe state.

Near-infrared (NIR; 600-900 nm) fluorescence detection has the effectiveness and advantage of penetrating through the skin to a deep thickness, and enables diagnosis in real time using a non-invasive method in vivo. In addition, near-infrared fluorescence detection has advantages of incurring lower costs than conventional SPECT and PET spectra and of high sensitivity owing to minimization of self-luminescence of tissues or cells. Nevertheless, it is still rarely used in animal models for early-stage Alzheimer's diagnosis.

Against this background, as a result of extended efforts to develop a novel compound effective as a near-infrared fluorescent probe that selectively binds to tau aggregates to overcome the conventional problems of early diagnosis of tauopathy, including Alzheimer's disease, the present inventors developed a novel quinoline derivative compound having high selectivity for tau aggregates, a method of preparing the same, a tau-targeting near-infrared fluorescent probe including the compound, and a composition for detecting tau fiber proteins containing the same as an active ingredient, thereby completing the present invention.

The above information disclosed in this Background section is only for enhancement of understanding of the background of the invention, and therefore it may contain information that does not form the prior art that is already known in this country to a person of ordinary skill in the art.

PRIOR ART DOCUMENT

Patent Document (Patent Document 1) International Publication Pat. No. 2015-060365 (2015.04.30)
(Patent Document 2) Korean Patent No. 10-1749808 (2017.06.15)

(Patent Document 3) Korean Patent No. 10-1802672 (2017.11.22)

Non-Patent Document (Non-Patent Document 1) Hualong Fu. et. al., J. Med. Chem., 58(17), 6972-6983 (2015)

SUMMARY OF THE DISCLOSURE

The present invention has been made in an effort to solve the above-described problems associated with the prior art, and it is an object of the present invention to provide a novel quinoline derivative compound selectively binding to tau aggregates.

It is another object to provide a near-infrared fluorescent probe for detecting tau fiber proteins including the novel quinoline derivative compound.

It is another object to provide a composition for diagnosing tauopathy containing the near-infrared fluorescent probe for detecting tau fiber proteins as an active ingredient.

It is another object to provide a method for detecting tau aggregates in vitro or in vivo using the novel quinoline derivative compound.

It is another object to provide a method for preparing the novel quinoline derivative compound.

In one aspect, the present invention provides a quinoline derivative compound represented by the following Formula 1:

[Formula 1]

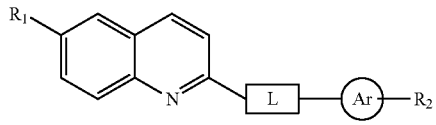

wherein

L is 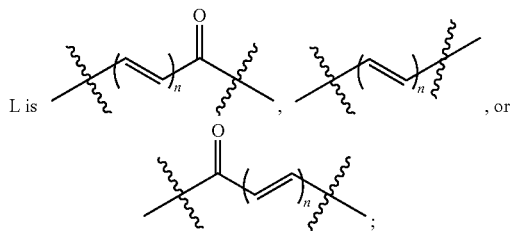, or

Ar is a $C_6$-$C_{10}$ aryl group or a $C_3$-$C_{10}$ heteroaryl group, $R_1$ is a $C_1$-$C_6$ alkyl group, a $C_1$-$C_6$ alkoxy group or a hydroxyl group, $R_2$ is a hydroxyl group, a halogen group, an amino group, a nitro group, a cyano group, a $C_1$-$C_6$ alkyl group, a $C_1$-$C_6$ alkenyl group, a $C_6$-$C_{10}$ aryl group, a $C_1$-$C_6$ alkoxy group, a $C_3$-$C_{10}$ heteroaryl group, or a $C_3$-$C_{10}$ heterocyclyl group, and n is an integer of 1 to 5, wherein the $C_1$-$C_6$ alkyl group includes at least one substituent group selected from the group consisting of hydrogen, a hydroxyl group, a halogen group, a $C_1$-$C_{13}$ alkyl group, a $C_1$-$C_6$ alkoxy group, an amide group (—(C=O)NR$_3$R$_4$), a $C_6$-$C_{10}$ aryl group, a $C_3$-$C_{10}$ heteroaryl group and a $C_3$-$C_{10}$ heterocyclyl group, the $C_6$-$C_{10}$ aryl group, the $C_3$-$C_{10}$ heteroaryl group or the $C_3$-$C_{10}$ heterocyclyl group includes at least one substituent group selected from the group consisting of hydrogen, a hydroxyl group, a halogen group, a carbonyl group (—(C=O)R$_3$R$_4$), a $C_1$-$C_3$ alkyl group substituted or unsubstituted with halogen or a $C_3$-$C_{10}$ heterocyclyl group, a $C_1$-$C_3$ alkoxy group substituted or unsubstituted with halogen or a $C_3$-$C_{10}$ heterocyclyl group, $C_6$-$C_{10}$ phenoxy, an amino group (—NR$_3$R$_4$), an amide group (—(C=O)NR$_3$R$_4$), a $C_6$-$C_{10}$ aryl group, a $C_3$-$C_{10}$ heteroaryl group and a $C_3$-$C_{10}$ heterocyclyl group, $R_3$ and $R_4$ described above include at least one substituent group selected from the group consisting of hydrogen, a $C_1$-$C_6$ alkyl group, a $C_1$-$C_6$ alkenyl group, a $C_1$-$C_6$ alkynyl group, a $C_6$-$C_{10}$ aryl group, a $C_3$-$C_{10}$ heteroaryl group and a $C_3$-$C_{10}$ heterocyclyl group, and the $C_3$-$C_{10}$ heteroaryl group and the $C_3$-$C_{10}$ heterocyclyl group include at least one heteroatom selected from the group consisting of N, O and S.

In another aspect, the present invention provides a near-infrared fluorescent (NIRF) probe for detecting a tau fiber protein including the quinoline derivative compound represented by the following Formula 1.

In another aspect, the present invention provides a composition containing the near-infrared fluorescent probe for detecting a tau fiber protein, as an active ingredient, wherein the composition is used for diagnosis of tauopathy selected from the group consisting of Alzheimer's disease, Parkinson's disease, progressive nuclear paralysis, corticobasal degeneration, argyrophilic grain disease, Pick's disease and frontotemporal dementia.

In another aspect, the present invention provides a method for detecting a tau aggregate in vitro or in vivo or ex vivo using the quinoline derivative compound represented by the following Formula 1.

In another aspect, the present invention provides a method for preparing the quinoline derivative compound represented by the following Formula 1.

Other aspects and preferred embodiments of the invention are discussed infra.

The above and other features of the invention are discussed infra.

BRIEF DESCRIPTION OF THE DRAWINGS

The above and other features of the present invention will now be described in detail with reference to certain exemplary embodiments thereof, illustrated in the accompanying drawings which are given hereinbelow by way of illustration only, and thus are not limitative of the present invention, and wherein:

FIG. 1 shows fluorescence spectrum changes and the degree of binding, particularly labeling ability to tau aggregates, in the absence of a target protein of a new synthetic compound in vitro (PBS) and in the presence of a non-aggregated tau protein (Tau Mono.), a tau fiber protein aggregate (Tau Agg.), a non-aggregated amyloid beta (Aβ Mono.), an amyloid beta aggregate (Aβ Agg.) and bovine serum albumin (BSA), and shows a fluorescence spectrum observed from Compounds 13a(FIG. 1a) ((E)-1-(4-(dimethylamino) phenyl)-3-(6-methoxyquinolin-2-yl)prop-2-en-1-one, Compound No. 1), 13d(FIG. 1b) ((E)-1-(4-(tolyl)-3-(6-methoxyquinolin-2-yl)prop-2-en-1-one, Compound No. 4), 13e(FIG. 1c) ((E)-1-(4-(bromophenyl)-3-(6-methoxyquinolin-2-yl)prop-2-en-1-one, Compound No. 5), 15g(FIG. 1d) (6-methoxy-24(1E,3E)-4-(3-nitrophenyl)buta-1,3-dien-1-yl)quinolone, Compound No. 9), 15h(FIG. 1e) (6-methoxy-2-((1E,3E)-4-(2,4-difluorophenyl)buta)-1,3-diene-1-yl)quinolone, Compound No. 10), 15b(FIG. 1f) (4-((1E,3E)-4-(6-methoxyquinolin-2-yl)buta-1,3-diene-1-yl)-N-methylaniline, Compound No. 11), 15e(FIG. 1g) (6-methoxy-2-((1E,3E)-4-(6-nitropyridin-3-yl)buta-1,3-dien-1-yl)quinolone, Compound No. 12), 15d(FIG. 1h) (54 (1E,3E)-4-(6-methoxyquinolin-2-yl)buta-1,3-dien-1-yl)-N,N-dimethylpyridin-2-amine, Compound No. 14), 16d(FIG. 1i) ((2E,4E)-5-(6-(dimethylamino)pyridin-3-yl)-1-(6-methoxyquinolin-2-yl)penta-2,4-diene-1-one, Compound No. 16) and ThS(FIG. 1j), when the tau monomer, tau aggregate, Aβ monomer, Aβ aggregate and bovine serum albumin (BSA) are each present at a concentration of 10 μM in PBS (phosphate-buffered saline).

DETAILED DESCRIPTION

Figure 1A:
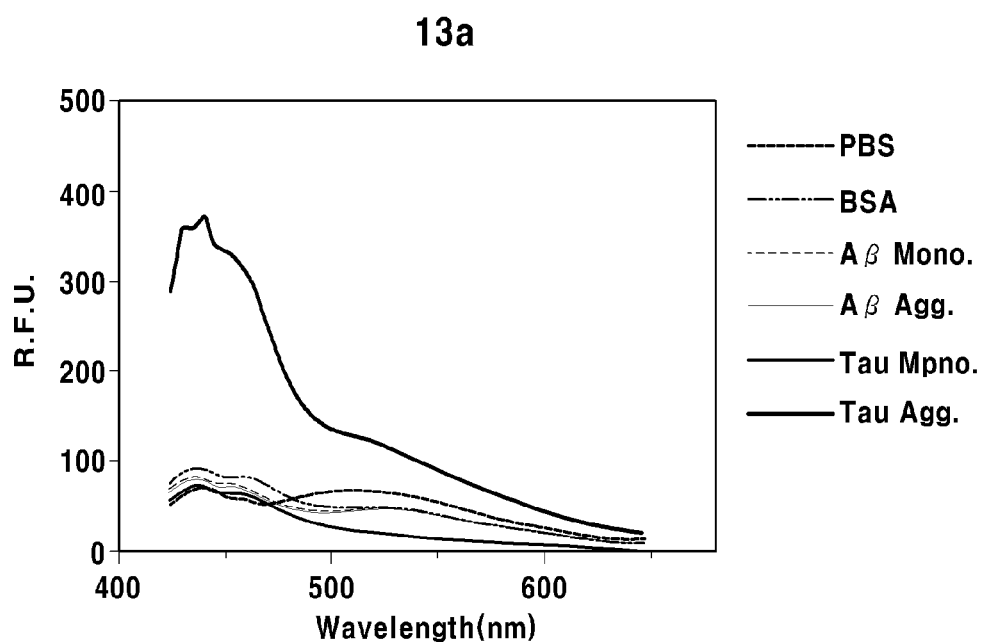
FIG. 1 shows the degree of binding to tau aggregates and amyloid beta aggregates of a novel synthetic compound according to an embodiment of the present invention, which can be used as an imaging fluorescence probe for selectively distinguishing tau aggregates in vitro. Specifically.

Unless the context clearly indicates otherwise, all numbers, figures and/or expressions that represent ingredients, reaction conditions, polymer compositions and amounts of mixtures used in the specification are approximations that reflect various uncertainties of measurement occurring inherently in obtaining these figures, among other things. For this reason, it should be understood that, in all cases, the term "about" should modify all the numbers, figures and/or expressions. In addition, when numerical ranges are disclosed in the description, these ranges are continuous and include all numbers from the minimum to the maximum including the maximum within the range unless otherwise defined. Furthermore, when the range refers to an integer, it includes all integers from the minimum to the maximum including the maximum within the range, unless otherwise defined.

It should be understood that, in the specification, when a range is referred to regarding a parameter, the parameter encompasses all figures including end points disclosed within the range. For example, the range of "5 to 10" includes figures of 5, 6, 7, 8, 9, and 10, as well as arbitrary sub-ranges, such as ranges of 6 to 10, 7 to 10, 6 to 9, and 7 to 9, and any figures, such as 5.5, 6.5, 7.5, 5.5 to 8.5 and 6.5 to 9, between appropriate integers that fall within the range. In addition, for example, the range of "10% to 30%" encompasses all integers that include numbers such as 10%, 11%, 12% and 13% as well as 30%, and any sub-ranges of 10% to 15%, 12% to 18%, or 20% to 30%, as well as any numbers, such as 10.5%, 15.5% and 25.5%, between appropriate integers that fall within the range.

Also, the terms and abbreviations used herein may be interpreted as having meanings commonly understood by those skilled in the art to which the present invention pertains unless otherwise defined.

Hereinafter, the present invention will be described in detail.

As a result of extended efforts to develop a novel compound effective as a near-infrared fluorescent probe that selectively binds to tau aggregates to overcome the conventional problems of early diagnosis of tauopathy including Alzheimer's disease, the present inventors developed a novel quinoline derivative compound having high selectivity for tau aggregates, a method of preparing the same, a tau-targeting near-infrared fluorescent probe including the compound, and a composition for detecting tau fiber proteins containing the same as an active ingredient.

In one aspect, the present invention provides a quinoline derivative compound represented by the following Formula 1:

[Formula 1]

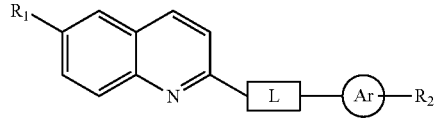

wherein

L is 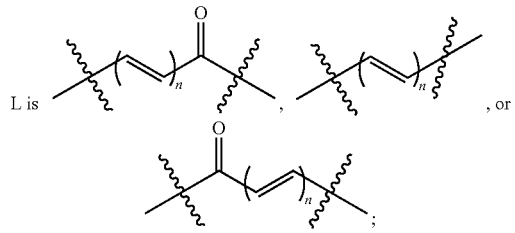, or

Ar is a $C_6$-$C_{10}$ aryl group or a $C_3$-$C_{10}$ heteroaryl group,
$R_1$ is a $C_1$-$C_6$ alkyl group, a $C_1$-$C_6$ alkoxy group or a hydroxyl group,
$R_2$ is a hydroxyl group, a halogen group, an amino group, a nitro group, a cyano group, a $C_1$-$C_6$ alkyl group, a $C_1$-$C_6$ alkenyl group, a $C_6$-$C_{10}$ aryl group, a $C_1$-$C_6$ alkoxy group, a $C_3$-$C_{10}$ heteroaryl group, or a $C_3$-$C_{10}$ heterocyclyl group, and
n is an integer of 1 to 5,
wherein the $C_1$-$C_6$ alkyl group includes at least one substituent group selected from the group consisting of hydrogen, a hydroxyl group, a halogen group, a $C_1$-$C_{13}$ alkyl group, a $C_1$-$C_6$ alkoxy group, an amide group (—(C═O)NR$_3$R$_4$), a $C_6$-$C_{10}$ aryl group, a $C_3$-$C_{10}$ heteroaryl group and a $C_3$-$C_{10}$ heterocyclyl group,
the $C_6$-$C_{10}$ aryl group, the $C_3$-$C_{10}$ heteroaryl group or the $C_3$-$C_{10}$ heterocyclyl group includes at least one substituent group selected from the group consisting of hydrogen, a hydroxyl group, a halogen group, a carbonyl group (—(C═O)R$_3$R$_4$), a $C_1$-$C_3$ alkyl group substituted or unsubstituted with halogen or a $C_3$-$C_{10}$ heterocyclyl group, a $C_1$-$C_3$ alkoxy group substituted or unsubstituted with halogen or a $C_3$-$C_{10}$ heterocyclyl group, $C_6$-$C_{10}$ phenoxy, an amino group (—NR$_3$R$_4$), an amide group (—(C═O)NR$_3$R$_4$), a $C_6$-$C_{10}$ aryl group, a $C_3$-$C_{10}$ heteroaryl group and a $C_3$-$C_{10}$ heterocyclyl group,
$R_3$ and $R_4$ described above include at least one substituent group selected from the group consisting of hydrogen, a $C_1$-$C_6$ alkyl group, a $C_1$-$C_6$ alkenyl group, a $C_1$-$C_6$ alkynyl group, a $C_6$-$C_{10}$ aryl group, a $C_3$-$C_{10}$ heteroaryl group and a $C_3$-$C_{10}$ heterocyclyl group, and
the $C_3$-$C_{10}$ heteroaryl group and the $C_3$-$C_{10}$ heterocyclyl group include at least one heteroatom selected from the group consisting of N, O and S.

Ar described above is substituted or unsubstituted benzene, substituted or unsubstituted pyridazine, substituted or unsubstituted pyrazine, substituted or unsubstituted imidazole, substituted or unsubstituted pyrazole, substituted or unsubstituted furan, substituted or unsubstituted pyrimidine, substituted or unsubstituted pyrrole, substituted or unsubstituted pyridine, substituted or unsubstituted indole, substituted or unsubstituted thiazole, or substituted or unsubstituted benzothiazole, $R_1$ described above is any one selected from a $C_1$-$C_3$ alkyl group, a $C_1$-$C_3$ alkoxy group and a hydroxyl group, and n is an integer of 1 or 2.

In one aspect of the present invention, the compound includes a quinoline derivative compound which is represented by the following Formula 1 and selected from the group consisting of the following Compound Nos. 1 to 18:

(Compound No. 1 (E)-1-(4-(dimethylamino)phenyl)-3-(6-methoxyquinolin-2-yl)prop-2-en-1-one, (Compound No. 2) (E)-1-(4-(tert-butoxycarboxamino)phenyl)-3-(6-methoxyquinolin-2-yl)prop-2-en-1-one (Compound No. 3) (E)-1-4-(Aminophenyl)-3-(6-hydroxyquinolin-2-yl)prop-2-en-1-one, (Compound No. 4) (E)-1-(4-Tolyl)-3-(6-methoxyquinolin-2-yl)prop-2-en-1-one, (Compound No. 5) (E)-1-(4-Bromophenyl)-3-(6-methoxyquinolin-2-yl)prop-2-en-1-one, (Compound No. 6) (E)-6-methoxy-2-(4-(trifluoromethyl)styryl)quinolone;

(Compound No. 7) (E)-6-methoxy-2-(2-(pyridin-4-yl)vinyl)quinolone;

(Compound No. 8) 6-methoxy-2-((1E,3E)-4-(3-chlorophenyl)buta-1,3-dien-1-yl)quinolone, (Compound No. 9) 6-methoxy-2-((1E,3E)-4-(3-nitrophenyl)buta-1,3-dien-1-yl)quinolone, (Compound No. 10) 6-methoxy-2-((1E,3E)-4-(2,4-difluorophenyl)buta-1,3-dien-1-yl)quinolone, (Compound No. 11) 4-((1E,3E)-4-(6-methoxyquinolin-2-yl)buta-1,3-diene-1-yl)-N-methylanaline, (Compound No. 12) 6-methoxy-2-((1E,3E)-4-(6-nitropyridin-3-yl)buta-1,3-dien-1-yl)quinolone, (Compound No. 13) 4-((1E,3E)-4-(6-methoxyquinolin-2-yl)buta-1,3-diene-1-yl)-N,N-dimethylaniline, (Compound No. 14) 5-((1E,3E)-4-(6-methoxyquinolin-2-yl)buta-1,3-dien-1-yl)-N,N-dimethylpyridin-2-amine;

(Compound No. 15) (2E,4E)-5-(4-(dimethylamino)phenyl)-1-(6-methoxyquinolin-2-yl)penta-2,4-dien-1-one (Compound No. 16) (2E,4E)-5-(6-(dimethylamino)pyridin-3-yl)-1-(6-methoxyquinolin-2-yl)penta-2,4-diene-1-one, (Compound No. 17) (2E,4E)-1-(6-methoxyquinolin-2-yl)-5-(4-(methylamino)phenyl)penta-2,4-dien-1-one, and (Compound No. 18) (2E,4E)-5-(44(2-hydroxyethyl)(methyl)amino)phenyl)-1-(6-methoxyquinolin-2-yl)penta-2,4-dien-1-one.

As used herein, the term "substitution" means that, when one or more hydrogen atoms in an organic compound are replaced with another atomic group to form a derivative, the other atomic group is introduced in place of a hydrogen atom, and the term "substituent" refers to an atomic group introduced at this time.

Examples of the substituent include halogen atoms, $C_1$-$C_{20}$ alkyl groups substituted with a halogen atom (e.g., $CCF_3$, $CHCF_2$, $CH_2F$ or $CCl_3$), $C_1$-$C_{20}$ alkoxy, $C_1$-$C_2$Dalkoxyalkyl, a hydroxy group, a nitro group, a cyano group, an amino group, an amidino group, hydrazine, hydrazone, a carboxyl group or salt thereof, a sulfonyl group, a sulfamoyl group, a sulfonic acid group or salt thereof, a phosphoric acid or salt thereof, and a $C_1$-$C_{20}$ alkyl group, a $C_2$-$C_{20}$ alkenyl group, a $C_2$-$C_{20}$ alkynyl group, a $C_1$-$C_{20}$ heteroalkyl group, a $C_6$-$C_{20}$ aryl group, a $C_6$-$C_{20}$ arylalkyl group, a $C_6$-$C_{20}$ heteroaryl group, a $C_7$-$C_{20}$ heteroarylalkyl group, a $C_6$-$C_{20}$ heteroaryloxy group, a $C_6$-$C_{20}$ heteroaryloxyalkyl group or a $C_6$-$C_{20}$ heteroarylalkyl group. In the definition of substituents in the present invention, the term "alkyl" means an aliphatic hydrocarbon radical. The alkyl may be a saturated alkyl that does not contain an alkenyl or alkynyl moiety, or an unsaturated alkyl that contains at least one alkenyl or alkynyl moiety. The term "alkenyl" means a group containing at least one carbon-carbon double bond, and the term "alkynyl" means a group containing at least one carbon-carbon triple bond. The alkyl may have a cyclic, branched or straight-chain form when used alone or in combination.

The term "aryl" means an aromatic monocyclic group containing 6 carbon atoms, which may be further fused, either alone or in combination with another radical, with a second 5- or 6-membered carbocyclic group, which may be aromatic, saturated or unsaturated. Examples of aryls may include, but are not limited to, phenyl, indanyl, 1-naphthyl, 2-naphthyl, tetrahydronaphthyl and the like. The aryl may be linked to another group at an appropriate position on the aromatic ring.

The term "alkoxy" refers to an alkyl group (i.e., —O-alkyl) linked to another group via an oxygen atom. The alkoxy group may or may not be substituted with at least one appropriate substituent. Examples of the alkoxy group include, but are not limited to, ($C_1$-06) alkoxy groups such as —O-methyl, —O-ethyl, —O-propyl, —O-isopropyl, —O-2-methyl-1-propyl, —O-2-methyl-2-propyl, —O-2-methyl-1-butyl, —O-3-methyl-1-butyl, —O-2-methyl-3-butyl, —O-2,2-dimethyl-1-propyl, —O-2-methyl-1-pantyl,-3-O-methyl-1-pantyl, —O-4-methyl-1-pantyl, —O-2-methyl-2-pentyl, —O-3-methyl-2-pentyl, —O-4-methyl-2-pentyl, —O-2,2-dimethyl-1-butyl, —O-3,3-dimethyl-butyl, —O-2-ethyl-1-butyl, —O-butyl, —O-isobutyl, —O-t-butyl, —O-pentyl, —O-isopentyl, —O-neopentyl and —O-hexyl.

The term "phenoxy" means a phenyl group (i.e., —O-aryl) linked to another group via an oxygen atom. The phenoxy group may or may not be substituted with at least one halogen; an alkyl group; an aryl group; and a heteroaryl group, but is not limited thereto.

The term "amino group" means an alkyl group linked to another group via a nitrogen atom (i.e., —NH— or —N-alkyl). The amino group may or may not be substituted with at least one appropriate substituent. Examples of the amino group include, but are not limited to, ($C_1$-06) amino groups, such as —NH-methyl, —NH-ethyl, —NH-propyl, —NH-isopropyl, —NH-2-methyl-1-propyl, —NH-2-methyl-2-propyl, —NH-2-methyl-1-butyl, —NH-3-methyl-1-butyl, —NH-2-methyl-3-butyl, —NH-2,2-dimethyl-1-propyl, —NH-2-methyl-1-pentyl, 3-N H-methyl-1-pentyl, —NH-4-methyl-1-pentyl, —NH-2-methyl-2-pentyl, —NH-3-methyl-2-pentyl, —NH-4-methyl-2-pentyl, —NH-2,2-dimethyl-1-butyl, —NH-3,3-dimethyl-butyl, —NH-2-ethyl-1-butyl, —NH-butyl, —NH-isobutyl, —NH-t-butyl, —NH-pentyl, —NH-isopentyl, —NH-neopentyl, —NH-hexyl, —N, N-dimethyl, —N-methyl-N-ethyl, —N-methyl-N-propyl, —N-methyl-isopropyl, —N-methyl-N-butyl, —N-methyl-N-isobutyl, —N-methyl-N-pentyl, —N-methyl-N-isopentyl, N-methyl-N-hexyl, N-methyl-N-isohexyl, —N, N-diethyl, —N-ethyl-N-propyl, —N-ethyl-N-isopropyl, —N-ethyl-N-butyl, —N-ethyl-N-isobutyl, —N-ethyl-N-pentyl, —N-ethyl-N-isopentyl, —N-ethyl-N-hexyl, —N-ethyl-N-isohexyl, —N, N-di propyl, —N-propyl-N-isopropyl, —N-propyl-N-butyl, —N-propyl-N-isobutyl, —N-propyl-N-pentyl, —N-propyl-N-isopentyl, —N-propyl-N-hexyl, —N-propyl-N-isohexyl, —N, N-dibutyl, —N-butyl-N-isobutyl, —N-butyl-N-pentyl, —N-butyl-N-isopentyl, —N-butyl-N-hexyl, —N-butyl-N-isohexyl, —N,N-dipentyl, -N-pentyl-N-hexyl, -N-pentyl-N-isohexyl, and —N, N-dihexyl.

The term "halogen atom" means fluorine (F), chlorine (Cl), bromine (Br) or iodine (I).

The term "carbonyl group" means —(C=O)—, and may be substituted with hydrogen, an alkyl group, an alkoxy group and an amino group, but is not limited thereto.

The term "heterocycle group" means a heteroaromatic compound containing at least one hetero atom selected from the group consisting of N, O, and S, unless otherwise mentioned. Preferably, the heterocyclic group may include a pyrrolidine group, a furan group, a morpholine group, a piperazine group and a piperidine group, and more preferably a pyrrolidine group, a piperidine group, a piperazine group and a morpholine group, but is not limited thereto.

The term "heteroaryl group" means a heteroaromatic compound containing at least one hetero atom selected from the group consisting of N, O, and S, unless otherwise mentioned. Preferably, the heteroaryl group is a pyridine group, a pyrazine group, a pyrimidine group, a pyridazine group, a pyrazole group, an imidazole group, a triazole group, an indole group, an oxadiazole group, a thiadiazole group, a quinoline group, an isoquinoline group, an isoxazole group, an oxazole group, a thiazolyl group and a pyrrole group, but is not limited thereto.

The term "derivative" refers to a compound obtained by substituting a part of the structure of the compound with another atom or atomic group.

Specific examples of quinoline derivative compounds preferred as compounds according to the present invention are as follows:

[Compound No. 1) (E)-1-(4-(dimethylamino)phenyl)-3-(6-methoxyquinolin-2-yl)prop-2-en-1-one (Compound 13a)];

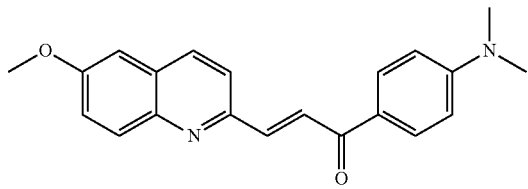

[Compound No. 2)

(E)-1-(4-(tert-butoxycarboxamino)phenyl)-3-(6-methoxyquinolin-2-yl)prop-2-en-1-one (Compound 13b)];

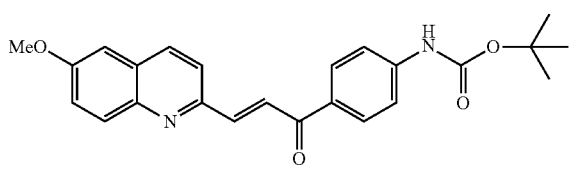 [SMILES: COc1ccc2nc(/C=C/C(=O)c3ccc(NC(=O)OC(C)(C)C)cc3)ccc2c1]

[Compound No. 3) (E)-1-(4-aminophenyl)-3-(6-hydroxyquinolin-2-yl)prop-2-en-1-one (Compound 13c)];

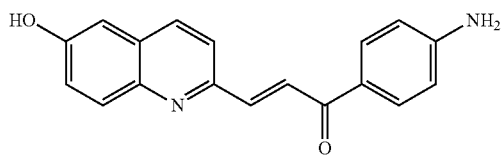 [SMILES: Nc1ccc(C(=O)/C=C/c2ccc3cc(O)ccc3n2)cc1]

[Compound No. 4: (E)-1-(4-tolyl)-3-(6-methoxyquinolin-2-yl)prop-2-en-1-one
(Compound 13d)];

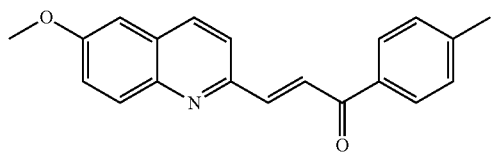

[Compound No. 5) (E)-1-(4-bromophenyl)-3-(6-methoxyquinolin-2-yl)prop-2-en-1-one (Compound 13e)];

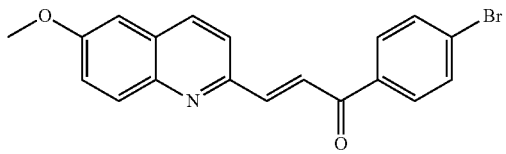 [SMILES: COc1ccc2nc(/C=C/C(=O)c3ccc(Br)cc3)ccc2c1]

[Compound No. 6: (E)-6-methoxy-2-(4-(trifluoromethyl)styryl)quinolone (Compound 14a)];

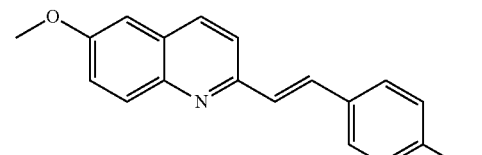

[Compound No. 7: (E)-6-methoxy-2-(2-(pyridin-4-yl)vinyl)quinolone (Compound 14b)];

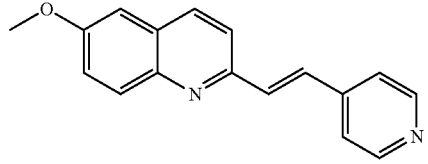 [SMILES: COc1ccc2nc(/C=C/c3ccncc3)ccc2c1]

[Compound No. 8) 6-methoxy-2-((/E,3E)-4-(3-chlorophenyl)buta-1,3-dien-1-yl)quinolone (Compound 15f)];

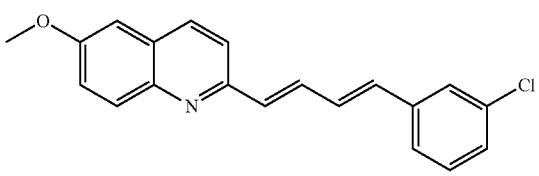 [SMILES: COc1ccc2nc(/C=C/C=C/c3cccc(Cl)c3)ccc2c1]

[Compound No. 9) 6-methoxy-2-((/E,3E)-4-(3-nitrophenyl)buta-1,3-dien-1-yl)quinolone (Compound 15g)];

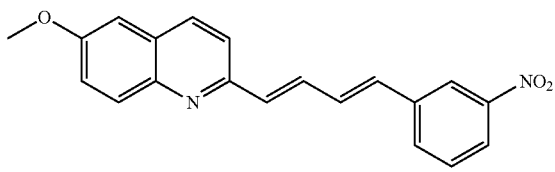 [SMILES: COc1ccc2nc(/C=C/C=C/c3cccc([N+](=O)[O-])c3)ccc2c1]

[Compound No. 10) 6-methoxy-2-((/E,3E)-4-(2,4-difluorophenyl)buta-1,3-dien-1-yl)quinolone (Compound 15h)];

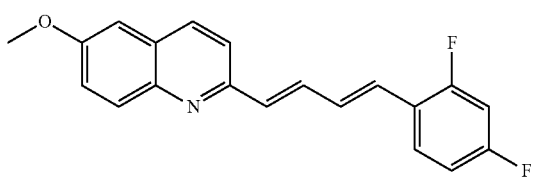 [SMILES: COc1ccc2nc(/C=C/C=C/c3ccc(F)cc3F)ccc2c1]

[Compound No. 11) 4-((/E,3E)-4-(6-methoxyquinolin-2-yl)buta-1,3-diene-1-yl)-N-methylanaline (Compound 15b)];

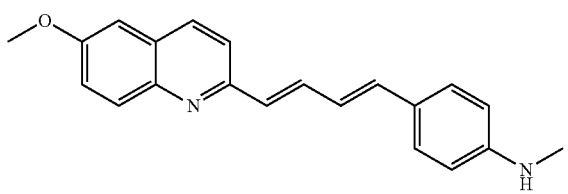

[Compound No. 12: 6-methoxy-2-((/E,3E)-4-(6-nitropyridin-3-yl)buta-1,3-dien-1-yl)quinolone (Compound 15e)];

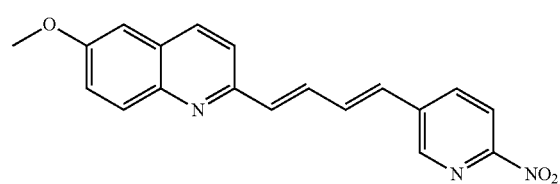 [SMILES: COc1ccc2nc(/C=C/C=C/c3ccc([N+](=O)[O-])nc3)ccc2c1]

[Compound No. 13: 4-((/E,3E)-4-(6-methoxyquinolin-2-yl)buta-1,3-diene-1-yl)-N,N-dimethylaniline (Compound 15c)]

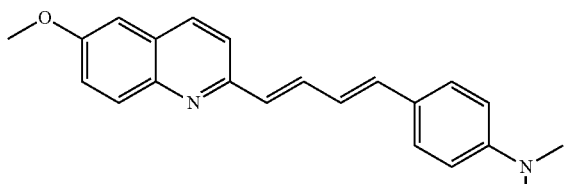

[Compound No. 14: 5-((1E,3E)-4-(6-methoxyquinolin-2-yl)buta-1,3-dien-1-yl)-N,N-dimethylpyridin-2-amine (Compound 15d)];

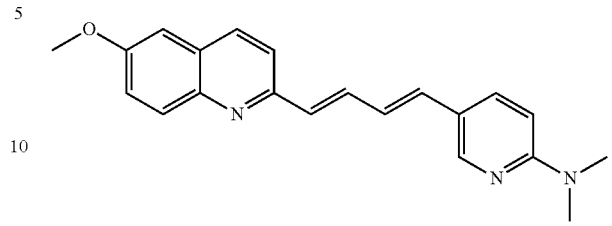

[Compound No. 15: (2E,4E)-5-(4-(dimethylamino)phenyl)-1-(6-methoxyquinolin-2-yl)penta-2,4-dien-1-one (Compound 16c)];

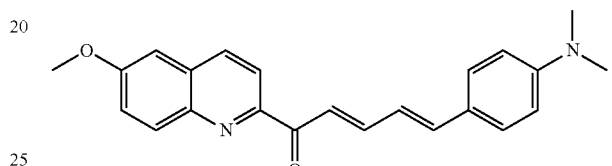

[Compound No. 16: (2E,4E)-5-(6-(dimethylamino)pyridin-3-yl)-1-(6-methoxyquinolin-2-yl)penta-2,4-diene-1-one (Compound 16d)];

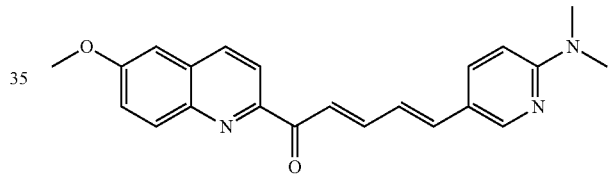

[Compound No. 17: (2E,4E)-1-(6-methoxyquinolin-2-yl)-5-(4-(methylamino)phenyl)penta-2,4-dien-1-one (Compound 16b)]; and

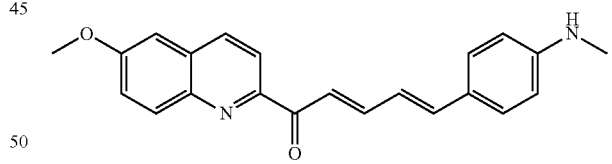

[Compound No. 18: (2E,4E)-5-(44(2-hydroxyethyl)(methyl)amino)phenyl)-1-(6-methoxyquinolin-2-yl)pent a-2,4-dien-1-one (Compound 16e)];

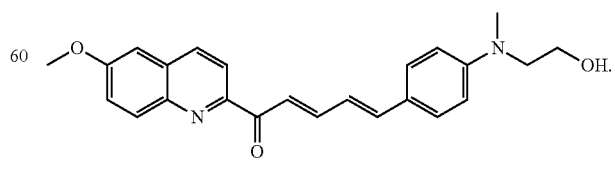

In another aspect, the present invention provides a near-infrared fluorescent (NIRF) probe for detecting a tau fiber protein containing the quinoline derivative compound represented by Formula 1 according to the present invention.

As used herein, the term "tau fiber protein" is a protein mainly involved in entanglement of nerve fibers associated with Alzheimer's disease, and a recent study has reported that there is a high possibility of the onset of dementia when the blood concentration of this substance is higher than a normal value for the same age group.

Meanwhile, the quinoline derivative compound according to the present invention is a self-fluorescent compound which selectively binds to a tau fiber protein to exhibit a strong tau fiber protein detection effect.

The fluorescent compound according to the present invention has excellent photophysical and photochemical properties such as full color-adjustable emission characteristics (fluorescence characteristics), Stokes shifts and drug-like lipid affinity with regard to membrane permeability within a single molecular structure through substituent changes.

Thus, the self-fluorescent compound of the present invention can be usefully as a fluorescent substance, a fluorescent dye or a near-infrared fluorescent probe in organic light-emitting devices, and in bio-imaging and other bio-applications, and can be used as a near-infrared fluorescent probe that is specifically capable of labeling a protein of interest in the field of immunocytochemistry.

In another aspect, the present invention provides a composition for diagnosing tauopathy containing the near-infrared fluorescent probe for detecting tau fiber proteins as an active ingredient.

The composition for early diagnosis of tauopathy containing the near-infrared fluorescent probe for detecting tau fiber proteins as an active ingredient according to the present invention can be used as a composition for early diagnosis of tauopathy selected from the group consisting of Alzheimer's disease, Parkinson's disease, progressive nuclear paralysis, corticobasal degeneration, argyrophilic grain disease, Pick's disease, and fronto-temporal dementia.

As used herein, the term "tauopathy" refers to a family of neurodegenerative diseases characterized by a malfunction of a tau protein (family closely related to intracellular microtubule-related proteins). These neurodegenerative diseases (tauopathy) include, for example, Alzheimer's disease, Parkinson's disease, progressive supranuclear palsy, corticobasal degeneration, argyrophilic grain diseases, Pick's disease and fronto-temporal dementia.

As described above, the near-infrared fluorescent probe for detecting tau fiber proteins includes the quinoline derivative compound represented by Formula 1, and the near-infrared fluorescent probe can be used for the diagnosis of related diseases caused by tau aggregates, that is, tauopathy, through specific binding of the compound with tau aggregates, fluorescence, and excellent lipid affinity thereof.

As used herein, the term "aggregate", which may be used interchangeably with "agglomerate", refers to a state in which various insoluble fibrous proteins are deposited and aggregated in a patient's tissue. In particular, the term "tau aggregate" means an aggregate formed by aggregation of tau fiber proteins, mainly involved in entanglement of nerve fibers.

The tau fiber protein detection is carried out by binding between the compound according to the invention and a Tau fiber protein aggregate, "binding" referring to a chemical interaction. Examples of such binding include covalent bonds, ionic bonds, hydrophilic-hydrophilic interactions, hydrophobic-hydrophobic interactions, and complex compound coordination.

The term "detection" includes not only determining whether or not tau aggregates are present in the sample (quantitative analysis), but also determining the amount thereof (quantitative analysis).

The composition may further include a pharmaceutically acceptable carrier, in addition to the quinoline derivative compound represented by Formula 1, for the diagnosis of tauopathy. The composition may be administered orally or parenterally during clinical administration, and may be used in the form of a general pharmaceutical preparation.

That is, the pharmaceutical composition according to the present invention may be administered in a variety of oral or parenteral formulations during actual clinical administration. The formulations may be prepared using conventionally used diluents or excipients such as fillers, extenders, binders, wetting agents, disintegrating agents and surfactants, which are commonly used in the art. Solid formulations for oral administration include tablets, pills, powders, granules, capsules and the like. These solid formulations may be prepared by mixing at least one excipient such as starch, calcium carbonate, sucrose, lactose or gelatin. In addition, lubricants such as magnesium stearate or talc are used in addition to simple excipients. Liquid formulations for oral administration include suspension agents, liquids/solutions, emulsions, syrups and the like. In addition to water and liquid paraffin, which are commonly used simple diluents, various excipients, such as wetting agents, sweeteners, fragrances and preservatives, may be contained therein. Formulations for parenteral administration may include sterile aqueous solutions, non-aqueous solvents, suspensions, emulsions, freeze-dried preparations, and suppositories. Non-aqueous solvents and suspension solvents include propylene glycol, polyethylene glycol, vegetable oils such as olive oil, and injectable esters such as ethyl oleate. As a base for suppositories, Witepsol, macrogol, tween 61, cacao butter, laurin butter and glycerogelatin may be used.

In another aspect, the present invention provides a method for detecting tau aggregates in cells in vitro or tissues ex vivo using the quinoline derivative compound represented by Formula 1 according to the present invention.

The method for detecting tau aggregates from in vitro cells or ex vivo tissue using the quinoline derivative compound represented by Formula 1 includes the following steps:

(a) administering a composition containing the near-infrared fluorescent probe for detecting tau fiber proteins as an active ingredient to cells in vitro or tissues ex vivo;
(b) binding the quinoline derivative compound represented by Formula 1 contained in the probe to the tau fiber proteins;
(c) emitting light with an excitation wavelength to the cells in vitro or the tissues ex vivo;
(d) detecting a fluorescent signal generated from the quinoline derivative compound represented by Formula 1;
(e) producing a graph or image showing the position and amount of the fluorescent signal; and
(f) determining a distribution and extent of tau aggregates in the cells in vitro or tissues ex vivo.

In step (a), the administering the composition to the cells in vitro or tissues ex vivo may be carried out by introducing a detectable amount of the composition containing the compound according to the present invention into the cells in vitro or tissues ex vivo. The introduction into the cells in vitro or tissues ex vivo is carried out by administering the compound into cells or tissues by methods known to those skilled in the art.

The cell may be, but is not limited to, a cell isolated from the brain, heart, blood vessels or arteries, and the tissue may be, but is not limited to, the brain, heart, blood vessels and arteries. The term "detectable amount" means the amount of a composition required for detection by a selected detection method. The amount of the composition introduced into cells in vitro or tissues ex vivo to be analyzed can be easily determined by those skilled in the art. For example, the composition can be administered to cells or tissues while increasing the amount of the composition until the active ingredient in the composition is detected by a selected detection method. Those skilled in the art can easily determine the time required for the compound according to the present invention to bind to tau aggregates after administering a detectable amount of the composition to the cells in vitro or tissues ex vivo and then detecting a fluorescent signal at various time points after administration.

In step (b), after a sufficient time for the compound to bind to the tau fiber protein, the fluorescent signal can be detected non-invasively in the cells in vitro or tissues ex vivo.

In step (c), the excitation wavelength may have a wavelength in the range of 300 to 500 nm, and the fluorescent signal generated in step (d) may have a wavelength in the range of 400 to 650 nm.

The fluorescence signal may be generated using a method of performing quantification and imaging in real time using a commercial spectrophotometer or a fluorescence microscope equipped with a software program capable of analyzing fluorescent signal data, but is not limited thereto.

The producing step in step (e) includes obtaining the acquired signal data through a software program installed in the spectrophotometer or fluorescent microscope and then producing a graph or image showing the location and amount of the fluorescent signal emitted by the compound from this data set.

The determining step in step (f) can be carried out by evaluating the resulting graph or image, because the emitted signal is directly related to the amount of tau aggregates.

Imaging tau aggregates in the brain has several potential advantages. Imaging techniques can improve diagnostic methods by identifying potential patients who have accumulated excess tau aggregates in the brain and thus are more likely to develop, for example, Alzheimer's disease. In addition, these techniques are expected to be useful, for example, in monitoring the progression of Alzheimer's disease. When drug therapy targeting tau proteins is possible, imaging of tau aggregates in the brain can provide an important means to monitor therapy.

The quinoline derivative compound represented by Formula 1 according to the present invention can be imaged using self-fluorescent properties even without the use of radioactive isotopes, and high-sensitivity detection is possible through high selective binding with tau aggregates.

In another aspect, the present invention provides a method of diagnosing a patient with a tau-aggregate-related disease.

The diagnostic method can also be used as a post-diagnosis method. The method for diagnosing a patient with a tau-aggregate-related disease further includes quantifying or imaging a tau fiber protein detected through the method for detecting tau aggregates, setting diagnostic criteria, and conducting diagnosis.

In another aspect, the present invention provides a method for producing the quinoline derivative compound represented by Formula 1.

The method includes any one of the following Reaction Scheme 1 to Reaction Scheme 3:

[Reaction Scheme 1]

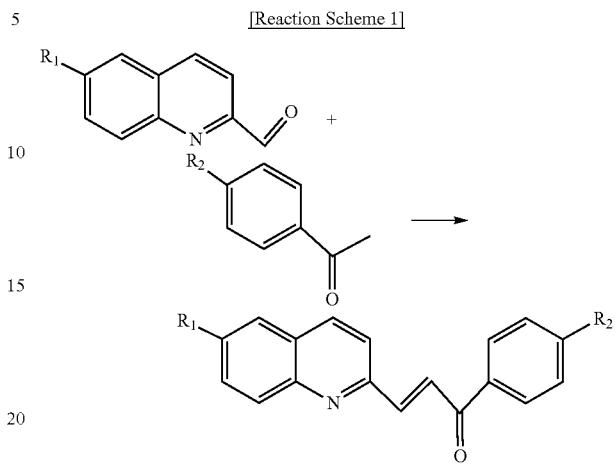

[Reaction Scheme 2]

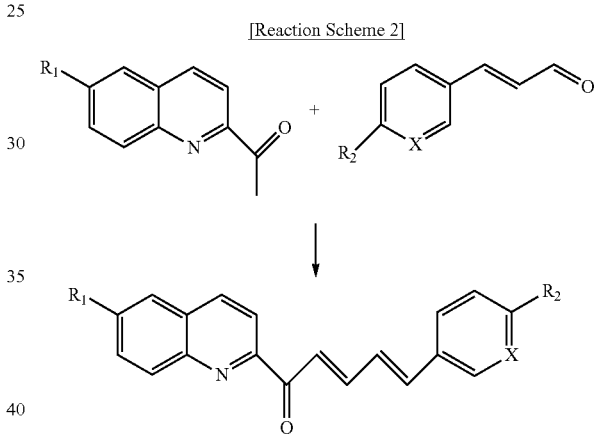

[Reaction Scheme 3]

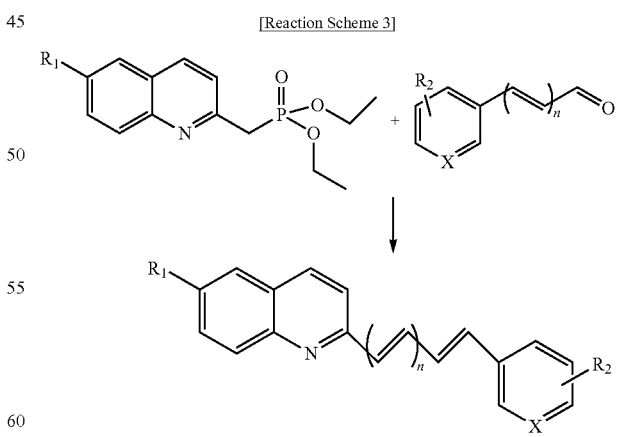

wherein in Reaction Scheme 1 to Reaction Scheme 3,
$R_1$ is a $C_1$-$C_6$ alkyl group, a $C_1$-$C_6$ alkoxy group or a hydroxyl group, and
$R_2$ is a hydroxyl group, a halogen group, an amino group, a nitro group, a cyano group, a $C_1$-$C_6$ alkyl group, a $C_1$-$C_6$ alkenyl group, a $C_6$-$C_{10}$ aryl group, a $C_1$-$C_6$ alkoxy group, a $C_3$-$C_{10}$ heteroaryl group, or a $C_3$-$C_{10}$ heterocyclyl group, wherein the $C_1$-$C_6$ alkyl group includes at least one substituent group selected from the group consisting of hydrogen, a hydroxyl group, a halogen group, a $C_1$-$C_{13}$ alkyl group, a $C_1$-$C_6$ alkoxy group, an amide group (—(C=O)NR$_3$R$_4$), a $C_6$-$C_{10}$ aryl group, a O3-O10 heteroaryl group and a $C_3$-$C_{10}$ heterocyclyl group, the $C_6$-$C_{10}$ aryl group, the $C_3$-$C_{10}$ heteroaryl group or the $C_3$-$C_{10}$ heterocyclyl group includes at least one substituent group selected from the group consisting of hydrogen, a hydroxyl group, a halogen group, a carbonyl group (—(C=O)R$_3$R$_4$), a $C_1$-$C_3$ alkyl group substituted or unsubstituted with halogen or a $C_3$-$C_{10}$ heterocyclyl group; a $C_1$-$C_3$ alkoxy group substituted or unsubstituted with halogen or a $C_3$-$C_{10}$ heterocyclyl group, a O6-O10 phenoxy, an amino group (-NR$_3$R$_4$), an amide group (—(C=O)NR$_3$R$_4$), a $C_6$-$C_{10}$ aryl group, a $C_3$-$C_{10}$ heteroaryl group and a $C_3$-$C_{10}$ heterocyclyl group, $R_3$ and $R_4$ described above include at least one substituent group selected from the group consisting of hydrogen, a $C_1$-$C_6$ alkyl group, a $C_1$-$C_6$ alkenyl group, a $C_1$-$C_6$ alkynyl group, a $C_6$-$C_{10}$ aryl group, a $C_3$-$C_{10}$ heteroaryl group, and a $C_3$-$C_{10}$ heterocyclyl group, and the $C_3$-$C_{10}$ heteroaryl group and $C_3$-$C_{10}$ heterocyclyl group include at least one heteroatom selected from the group consisting of N, O and S, in Reaction Scheme 2 and Reaction Scheme 3, X is N or CH, and in Reaction Scheme 3, n is an integer from 1 to 5.

Hereinafter, a specific example of a method for preparing the quinoline derivative compound represented by Formula 1 will be described.

The present invention includes a method for preparing the quinoline derivative compound represented by Formula 1, and the method includes a preparation process shown in Reaction Scheme 4, Reaction Scheme 5, and Reaction Scheme 6.

tion Scheme 4 is performed through a condensation reaction between the 6-methoxyquinoline-2-carboaldehyde compound represented by Formula 2 above and the p-substituted acetophenone represented by Formula 3 above.

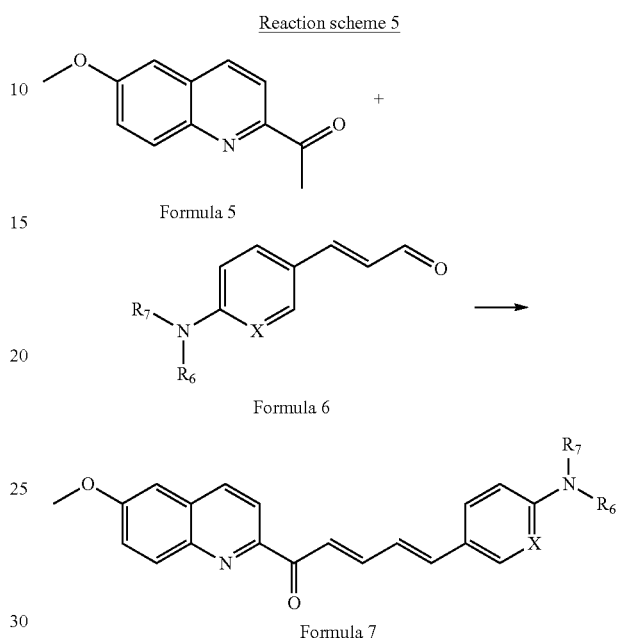

In Reaction Scheme 5, $R_6$ is selected from hydrogen, methyl and hydroxypropyl, and $R_7$ is selected from hydrogen, methyl and hydroxypropyl, wherein $R_6$ and $R_7$ are identical to or different from each other. The preparation method of Reaction Scheme 5 is performed through condensation between (E)-3-(3-/4-substituted phenyl)/(6-substituted pyridin-3-yl)acrylaldehyde, represented by Formula 6, and 1-(6-methoxyquinolin-2-yl)ethan-1-one, represented by Formula 5.

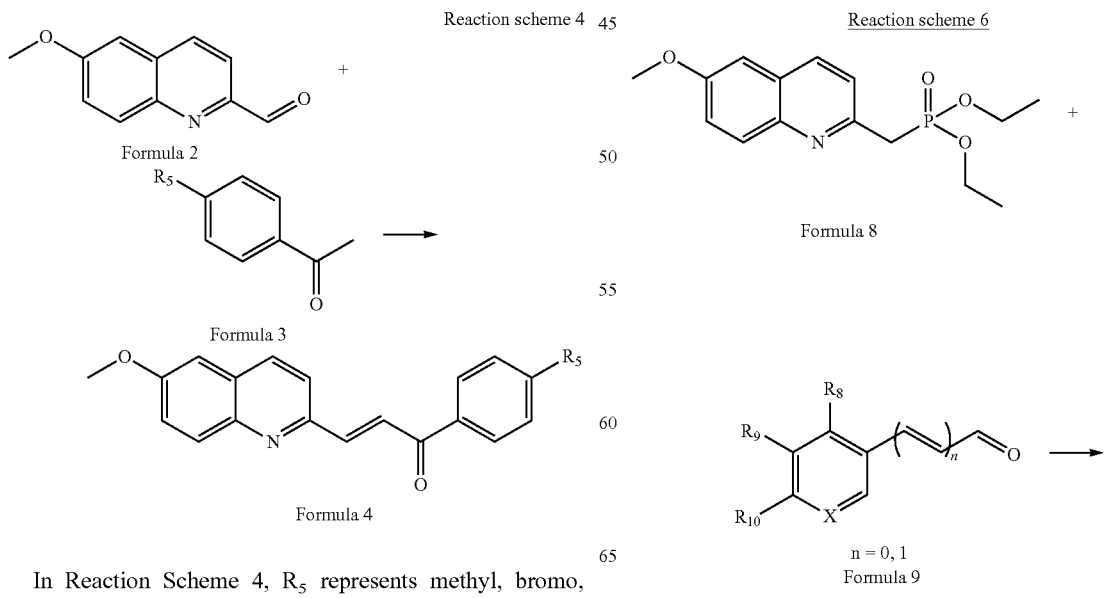

In Reaction Scheme 4, $R_5$ represents methyl, bromo, amino or dimethylamino. The preparation method of Reac-

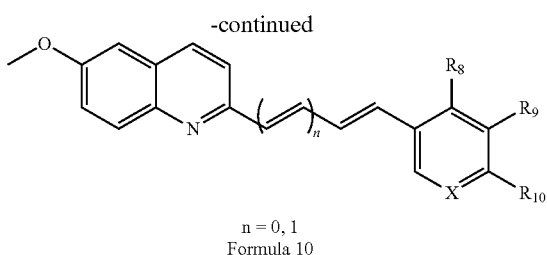

n = 0, 1
Formula 10

In Reaction Scheme 6, X is selected from carbon and nitrogen, and $R_8$, $R_9$ and $R_{10}$ are selected from hydrogen, halogen, nitro, amino, trifluoromethyl, methylamino and dimethylamino, wherein $R_8$, $R_9$ and $R_{10}$ are identical to or different from each other. The preparation method is performed through a condensation reaction between the (E)-3-(3-/4-substituted phenyl)/(6-substitutedpyridin-3-yl)acrylaldehyde compound, represented by Formula 9, and the diethyl (6-methoxyquinolin-2-yl)methyl)phosphonate compound, represented by Formula 8 above.

Reaction scheme 7

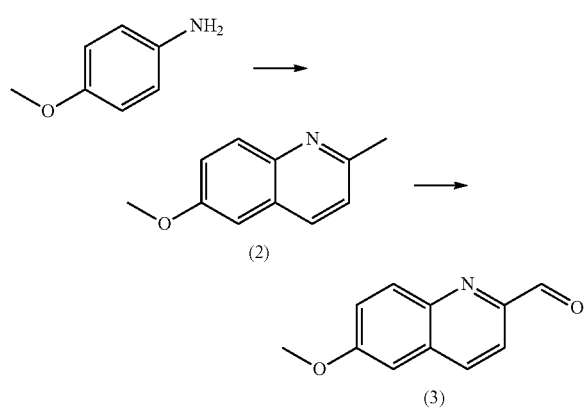

The aldehyde compound represented by Formula 2 used as a reactant according to the present invention was prepared as shown in Reaction Scheme 7. Specifically, the aldehyde Compound (3) was prepared by reacting croton aldehyde with p-methoxy aniline as a starting material at a high temperature under acidic conditions to prepare Compound (2), 6-methoxy-2-methylquinoline, followed by an oxidation reaction. Useful oxidizing agents include various organic oxidizing agents such as pyridinium chlorochromate (PCC), pyridinium dichromate (PDC), Dess-Martin-Periodinane (DMP), tetrapropylammonium perruthenate (TPAP), 2,2,6,6-tetramethyl-1-piperidinyloxy (TEMPO) and Swern oxidation reagents, as well as inorganic oxidizing agents such as potassium permanganate and selenium dioxide. Preferred is selenium dioxide.

Reaction scheme 8

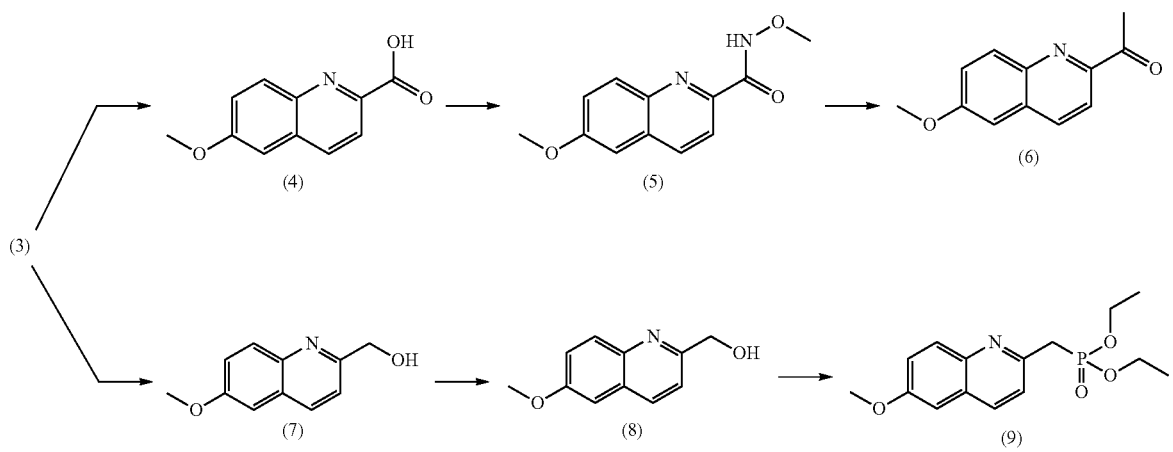

Compound (6), represented by Formula 5, and Compound (9), represented by Formula 8, were prepared by the method of Reaction Scheme 8. Specifically, the compound was prepared using Compound (3), prepared in the present invention, as a starting material. The aldehyde Compound (3) was converted to carboxylic acid Compound (4), Compound (4) was reacted with N,O-dimethylhydroxyamine is hydrochloride in the presence of a base and HATU (1-[bis(dimethylamino)methylene]-1H-1,2,3-triazolo[4,5-b]pyridinium 3-oxide hexafluorophosphate, hexafluorophosphate azabenzotriazole tetramethyl uronium) to prepare Compound (5), N,6-dimethoxy-N-methylquinoline-2-carboxamide, and then a Grignard reaction was conducted to prepare Compound (6). In addition, the aldehyde Compound (3) was converted to an alcohol Compound (7) through a reduction reaction, and then bromination was conducted to prepare Compound (8). The reducing agent is preferably sodium borohydride, which is selected from generally used alkyl metal reducing agents. Compound (8) was reacted with trialkylphosphite at a high temperature to prepare Compound (9), diethyl ((6-methoxyquinolin-2-yl)methyl)phosphonate. Here, the high temperature specifically means 100° C. to 150° C.

Reaction scheme 9

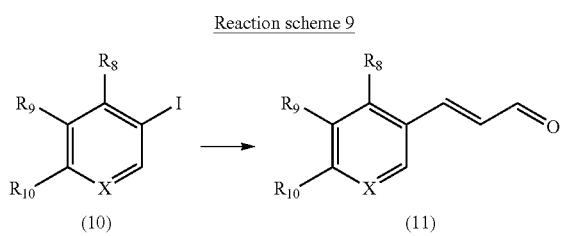

Among the compounds represented by Formula 9, Compound (11), corresponding to the case of n=1, was prepared by reacting allyl iodide (10) as a starting material with alkyl in the presence of a palladium catalyst using acrolein diethyl acetal.

Hereinafter, the present invention will be described in more detail with reference to Examples, Preparation Examples and Experimental Examples. However, the following Examples, Preparation Examples and Experimental Examples are provided only for illustration of the present invention, and should not be construed as limiting the scope of the present invention. It will be obvious to those skilled in the art that a variety of modifications and alterations are possible without departing from the ideas and scope of the present invention.

In addition, those skilled in the art to which the present invention pertains can prepare the target compound through various methods based on the structure of Formula 1, and these methods should be construed as falling within the scope of the present invention. That is, the compounds of the present invention can be prepared by arbitrarily combining the synthesis methods specifically described in the following Examples or various synthesis methods disclosed in the prior art, which are understood to fall within the scope of the present invention, and the method of preparing the compounds according to the present invention is not limited to the specific examples below.

EXAMPLE

Reference Example 1: 6-methoxy-2-methylquinoline (Compound 2)

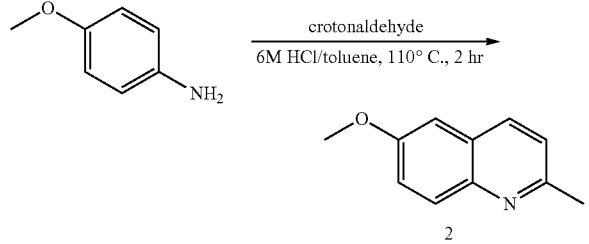

A mixture of 4-methoxy aniline (5 g, 40.5 mmol) and hydrochloric acid (6M, 100 mL) was reacted while heating at 110° C., and crotonaldehyde (5.69 g, 81 mmol) diluted in toluene (25 mL) was added dropwise thereto, followed by stirring for 2 hours. The reaction mixture was cooled to room temperature, separated from the water layer, neutralized with sodium carbonate ($Na_2CO_3$), extracted with ethyl acetate (3×50 mL), dried over anhydrous sodium sulfate ($Na_2SO_4$), and distilled under reduced pressure to remove the solvent. The residue was purified through silica gel column chromatography (elution solvent: ethyl acetate/n-hexane=1:5) to synthesize Compound 2 (4.6 g, 66%) as a white solid. $^1$H NMR (400 MHz, $CDCl_3$, 25° C., TMS) δ 7.97 (d, J=8.8 Hz, 1H), 7.94 (d, J=9.2 Hz, 1H), 7.36 (dd, J=2.8 Hz, J=9.2 Hz, 1H), 7.25 (s, 1H), 7.07 (d, J=2.8 Hz, 1H), 3.95 (S, 3H, $OCH_3$), 2.74 (s, 3H, $CH_3$)

Reference Example 2: 6-methoxyquinoline-2-carboaldehyde (Compound

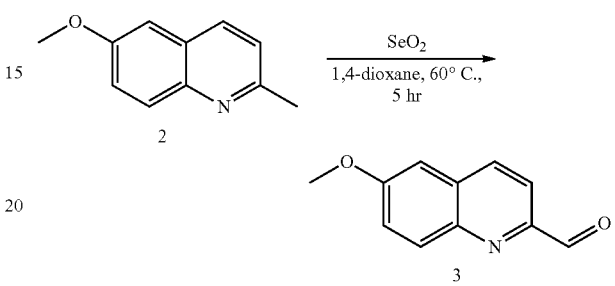

A solution of compound 2 (500 mg, 2.9 mmol) and selenium (IV) dioxide ($SeO_2$; 641 mg, 5.8 mmol) dissolved in 10 mL of dioxane (1,4-dioxane) as a solvent was stirred in a nitrogen atmosphere at a temperature of 60° C. for 5 hours. The reaction mixture was cooled to room temperature, filtered through celite and concentrated under reduced pressure, and the residue was purified through column chromatography (elution solvent: ethyl acetate/n-hexane=1:8) to obtain a white solid Compound 3 (438 mg, 81%).

$^1$H NMR (400 MHz, $CDCl_3$, 25° C., TMS) 510.21 (s, 1H, HC=O), 8.21 (d, J=8.8 Hz, 1H), 8.16 (d, J=9.2 Hz, 1H), 8.03 (d, J=8.4 Hz, 1H), 7.50 (dd, J=2.8 Hz, J=9.2 Hz, 1H), 7.17 (d, J=2.8 Hz, 1H), 4.00 (S, 3H, $OCH_3$)

Reference Example 3: 6-methoxyquinoline-2-carboxylic acid (Compound 4)

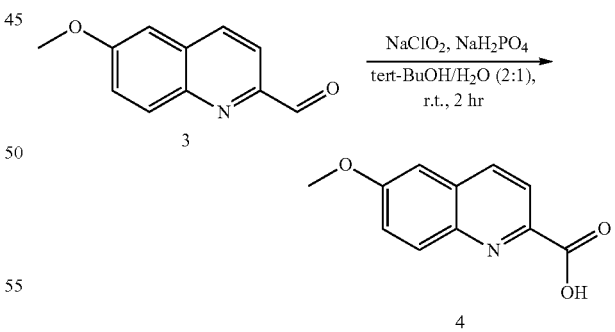

A solution of 6-methoxyquinoline-2-carboaldehyde (Compound 3) (0.8 g, 4.27 mmol) dissolved in tert-butanol (20 mL) was carefully added dropwise to a solution of sodium dihydrogen phosphate ($NaH_2PO_4$; 4.10 g, 34.2 mmol) and sodium chlorite ($NaClO_2$, 3.87 g, 42.7 mmol) in water (10 mL), followed by allowing to react at room temperature for 2 hours. The reaction mixture was adjusted to a pH of 4 and extracted with ethyl acetate (3×20 mL), the organic layer was dried over sodium sulfate ($Na_2SO_4$), and the desiccant was removed by filtration. Thereafter, the filtrate was concentrated under reduced pressure, and the obtained product, Compound 4 (865 mg, 100%) was used in the following Reference Example 4 reaction without purification.

Reference Example 4:
N,6-dimethoxy-N-methylquinoline-2-carboxamide (Compound 5)

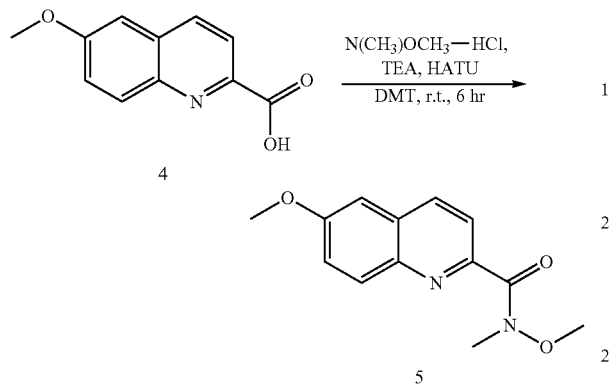

The carboxylic acid compound 4 (0.5 g, 2.46 mmol) prepared in Reference Example 3 above was dissolved in DMF (1 mL), and N,O-dimethylhydroxyamine hydrochloride (N(CH$_3$)OCH$_3$—HCl, 195 mg, 3.20 mmol), triethylamine (TEA; 747 mg, 7.38 mmol) and HATU (1.03 g, 2.71 mmol) were added thereto, and the reaction solution was stirred at room temperature for 6 hours. The reaction mixture was poured into water, extracted with ethyl acetate (3×20 mL) and dried over sodium sulfate (Na$_2$SO$_4$), and the solvent was concentrated under reduced pressure. Then, the residue was purified through column chromatography (elution solvent: hexane/ethyl acetate=1:1) to synthesize Compound 5 (390 mg, 64%) as a pale yellow solid.

$^1$H NMR (400 MHz, CDCl$_3$, 25° C., TMS) b 8.13 (d, J=8.8 Hz, 1H), 8.03 (d, J=9.2 Hz, 1H), 7.72 (brs, 1H), 7.41 (dd, J=2.8 Hz, J=9.2 Hz, 1H), 7.10 (d, J=2.4 Hz, 1H), 3.95 (s, 3H, OCH$_3$), 3.82 (s, 3H, OCH$_3$), 3.49 (s, 3H, NCH$_3$)

Reference Example 5:
1-(6-methoxyquinolin-2-yl)ethan-1-one (Compound 6)

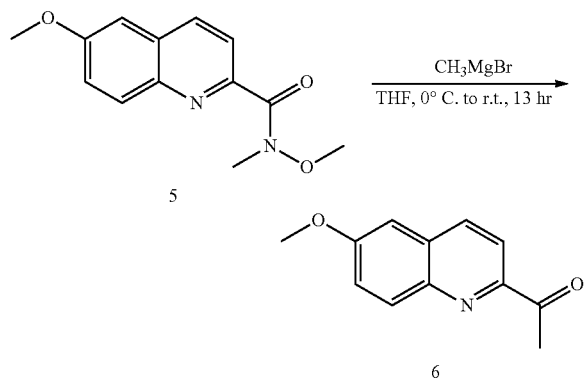

Methyl magnesium bromide (CH$_3$MgBr, 1.848 mL, 1.848 mmol, 1M in THF) was added dropwise at 0° C. to a solution of Compound 5 (350 mg, 1.42 mmol), prepared in Reference Example 4 dissolved in THF (10 mL), followed by reacting while stirring the mixture at 0° C. for 1 hour and at room temperature for 13 hours. The reaction mixture was diluted with water, extracted with ethyl acetate (3×20 mL), washed with brine, dried over sodium sulfate and distilled under reduced pressure to remove the solvent. The residue was purified through column chromatography (elution solvent: hexane/ethyl acetate=5:1) to synthesize Compound 6 (206 mg, 72%) as a light ivory solid.

$^1$H NMR (400 MHz, CDCl$_3$, 25° C., TMS) δ 8.12-8.07 (m, 3H), 7.42 (dd, J=2.8 Hz, J=9.2 Hz, 1H), 7.11 (d, J=2.8 Hz, 1H), 3.97 (s, 3H, OCH$_3$), 2.84 (s, 3H, CHs)

Reference Example 6:
(6-methoxyquinolin-2-yl)methanol (Compound 7)

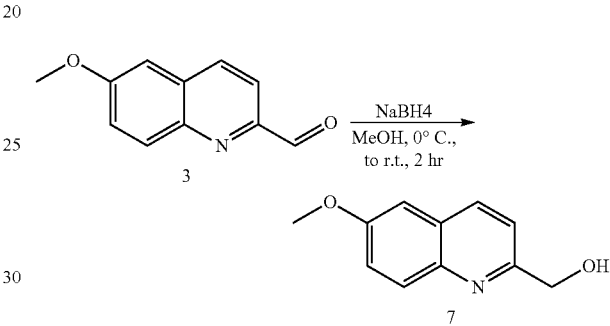

Compound 3 (1.00 g, 5.30 mmol) was dissolved in 25 mL of methanol, sodium borohydride (NaBH$_4$; 0.4 g, 10.6 mmol) was slowly added to the solution at 0° C., and the resulting mixture was reacted at room temperature for 2 hours. After completion of the reaction, methanol was removed under reduced pressure to obtain the target Compound 7 (1.00 g, 99%) as a white solid. $^1$H NMR (400 MHz, CDCl$_3$, 25° C., TMS) δ 8.07 (d, J=8.4 Hz, 1H), 8.00 (d, J=9.2 Hz, 1H), 7.40 (dd, J=2.8 Hz, J=9.2 Hz, 1H), 7.27 (d, J=8.8 Hz, 1H), 7.12 (d, J=2.8 Hz, 1H), 4.91 (s, 2H, CH$_2$-0), 4.37 (s, 1H, OH), 3.96 (s, 3H, OCH$_3$).

Reference Example 7:
2-(bromomethyl)-6-methoxyquinoline (Compound 8)

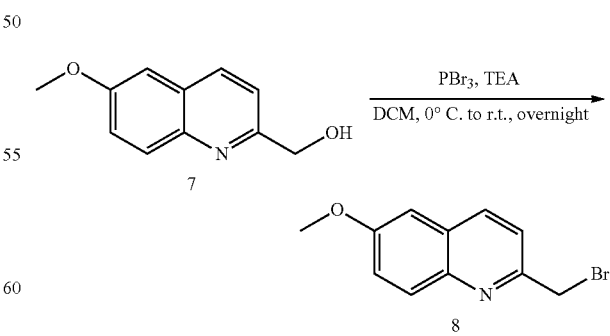

Compound 7 (0.95 g, 5.0 mmol), prepared in Reference Example 6, and triethylamine (TEA; 0.51 g, 5.0 mmol) were dissolved in anhydrous dichloromethane (DCM), phosphorus tribromide (PBr$_3$; 1.36 g, 5.0 mmol) was slowly added dropwise thereto at 0° C. in a nitrogen atmosphere, and the mixture was stirred at room temperature for 12 hours or longer (overnight). The reaction mixture was extracted with dichloromethane, washed with brine and dried over sodium sulfate ($Na_2SO_4$), and the solvent was concentrated under reduced pressure. Then, the residue was purified through a silica gel column (hexane/ethyl acetate=5:1) to prepare the target Compound 8 as a yellow solid (890 mg, 70%).

$^1$H NMR (400 MHz, $CDCl_3$, 25° C., TMS) δ 8.08 (d, J=8.4 Hz, 1H), 7.98 (d, J=9.2 Hz, 1H), 7.54 (d, J=8.4 Hz, 1H), 7.40 (dd, J=2.8 Hz, J=9.2 Hz, 1H), 7.09 (d, J=2.8 Hz, 1H), 4.72 (s, 2H, $CH_2Br$), 3.95 (s, 3H, $OCH_3$).

Reference Example 8: Diethyl ((6-methoxyquinolin-2-yl)methyl)phosphonate (Compound 9)

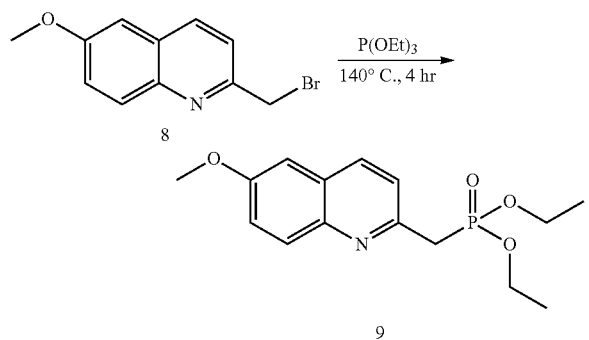

Compound 8 (500 mg, 2.0 mmol) obtained in Reference Example 7 and triethylphosphite (P(OEt)$_3$; 659 mg, 4.0 mmol) were reacted with stirring at 140° C. for 4 hours in a nitrogen atmosphere. Then, the solvent was distilled off and the residue was purified by silica gel column chromatography (dichloromethane/methanol=98:2) to prepare the target Compound 9 (435 mg, 71%) as a pale yellow solid.

$^1$H NMR (400 MHz, $CDCl_3$, 25° C., TMS) δ 8.00 (d, J=8.4 Hz, 1H), 7.93 (d, J=9.2 Hz, 1H), 7.48 (dd, J=1.6 Hz, J=8.4 Hz, 1H), 7.34 (dd, J=2.8 Hz, J=9.2 Hz, 1H), 7.05 (d, J=2.8 Hz, 1H), 4.08 (q, J=4.9 Hz, 4H), 3.91 (s, 3H, $OCH_3$), 3.59 (s, 1H, HCPO), 3.54 (s, 1H, HCPO), 1.25 (t, J=7.2 Hz, 6H).

Reference Example 9: (E)-3-(3-/4-substituted phenyl)/(6-substituted pyridin-3-yl)acrylaldehyde (Compounds 11a to 11a)

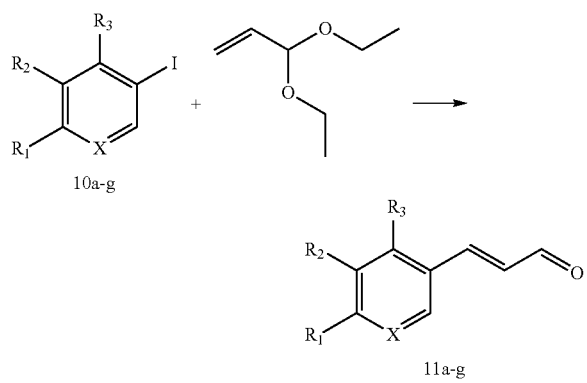

[General Preparation Method]

The allyl compound (0.5 mmol) of the substituent corresponding to iodide was dissolved in 2.0 mL of dimethylformamide, and acrolein diethyl acetal (1.5 mmol), TBAA (1 mmol), potassium carbonate (K2003; 0.75 mmol), KCl (0.5 mmol) and palladium acetate (0.015 mmol) were simultaneously added to the solution, followed by stirring at 90° C. for 2 hours. The reaction solution was cooled to room temperature, 2N hydrochloric acid was slowly added thereto, and the mixture was stirred at room temperature for 30 minutes and diluted with ethyl acetate. Then, the result was washed with water, the organic layer was dried over sodium sulfate ($Na_2SO_4$), the solvent was concentrated under reduced pressure, and the residue was purified through column chromatography (hexane/ethyl acetate) to prepare a target compound.

Tert-butyl (E)-methyl(4-(3-oxopro-1-en-1-yl)phenyl) carba mate (Compound 11a)

Orange solid, yield 25%. $^1$H NMR (400 MHz, $CDCl_3$, 25° C., TMS) b 9.69 (d, J=7.6 Hz, 1H, HC=O), 7.53 (d, J=8.8 Hz, 2H), 7.44 (d, J=15.6 Hz, 1H), 7.34 (d, J=8.8 Hz, 2H), 6.68 (dd, J=7.6 Hz, J=16.0 Hz, 1H), 3.30 (s, 3H, $NCH_3$), 1.48 (s, 9H).

(E)-3-(4-(dimethylamino)phenyl)acrylaldehyde (Compound 11 b)

Orange solid, yield 54%. $^1$H NMR (400 MHz, $CDCl_3$, 25° C., TMS) δ 9.60 (d, J=8.0 Hz, 1H, HC=O), 7.46 (d, J=9.2 Hz, 2H), 7.38 (d, J=15.6 Hz, 1H), 6.69 (d, J=9.2 Hz, 2H), 6.55 (dd, J=8.0 Hz, J=15.6 Hz, 1H), 3.06 (s, 6H, $N(CH_3)_2$).

(E)-3-(6-(dimethylamino)pyridin-3-yl)acrylaldehyde (Compound 11c)

Yellow powder, yield 33%. $^1$H NMR (400 MHz, $CDCl_3$, 25° C., TMS) b 9.61 (d, J=8.0 Hz, 1H, HC=O), 8.30 (d, J=2.4 Hz, 1H), 7.68 (dd, J=2.4 Hz, J=9.2 Hz, 1H), 7.37 (d, J=16.0 Hz, 1H), 6.55 (d, J=9.6 Hz, 1H), 6.54 (dd, J=8.0 Hz, J=16.0 Hz, 1H), 3.18 (s, 6H, $N(CH_3)_2$).

(E)-3-(6-nitropyridin-3-yl)acrylaldehyde (Compound 11d)

White powder, yield 28%. $^1$H NMR (400 MHz, $CDCl_3$, 25° C., TMS) b 9.82 (d, J=7.6 Hz, 1H, HC=O), 8.81 (d, J=2.0 Hz, 1H), 8.35 (d, J=8.4 Hz, 1H), 8.22 (dd, J=2.4 Hz, J=8.4 Hz, 1H), 7.58 (d, J=16.0 Hz, 1H), 6.89 (dd, J=7.2 Hz, J=16 Hz, 1H).

(E)-3-(3-chlorophenyl)acrylaldehyde (Compound 11e)

White solid, yield 55%. $^1$H NMR (400 MHz, $CDCl_3$, 25° C., TMS) b 9.74 (d, J=7.6 Hz, 1H, HC=O), 7.57 (d, J=1.6 Hz, 1H), 7.48 (d, J=1.6 Hz, 1H), 7.43-7.42 (m, 2H), 7.40 (d, J=15.6 Hz, 1H), 7.11 (dd, J=7.6 Hz, J=16 Hz, 1H).

(E)-3-(3-nitrophenyl)acrylaldehyde (Compound 11f)

White solid, yield 67%. $^1$H NMR (400 MHz, $CDCl_3$, 25° C., TMS) δ 9.81 (d, J=7.6 Hz, 1H, HC=O), 8.46 (s, 1H), 8.34 (d, J=8.0 Hz, 1H), 7.93 (d, J=8.0 Hz, 1H), 7.68 (t, J=8.0 Hz, 1H), 7.57 (d, J=16.0 Hz, 1H), 6.86 (dd, J=7.4 Hz, J=16 Hz, 1H).

(E)-3-(2,4-difluorophenyl)acrylaldehyde (Compound 11g)

White solid, yield 62%. $^1$H NMR (400 MHz, CDCl$_3$, 25° C., TMS) δ 9.71 (d, J=8.0 Hz, 1H, HC=O), 7.61 (d, J=8.4 Hz, 1H), 7.59 (d, J=16.0 Hz, 1H), 6.99-6.95 (m, 1H), 6.94-6.88 (m, 1H), 6.74 (dd, J=7.6 Hz, J=16.4 Hz, 1H).

Example 1

(E)-1-(4-(dimethylamino)phenyl)-3-(6-methoxyquinolin-2-yl)prop-2-en-1-one (Compound 13a) [Compound No. 1]

General preparation method of (E)-1-(4-substituted phenyl)-3-(quinon)-2-yl)prop-2-en-1-one

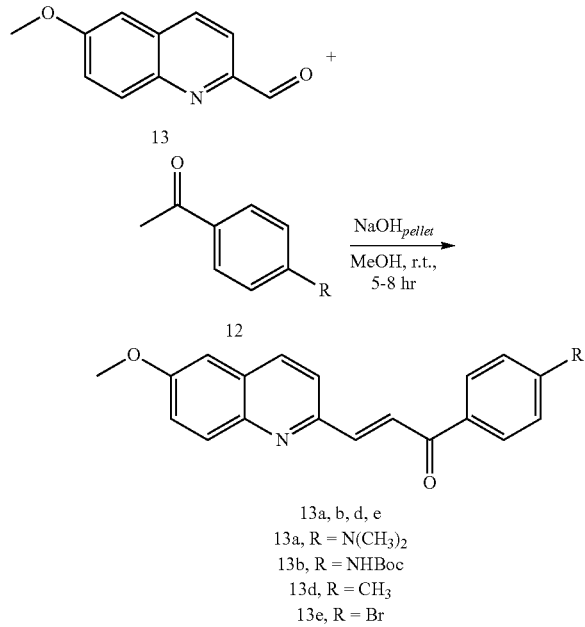

The aldehyde Compound 3 (1.0 mmol), prepared in Reference Example 2, and p-substituted acetophenone were dissolved in minimal methanol (2 to 4 mL), solid NaOH (~100 mg) was added to the solution, and the reaction mixture was reacted with stirring at room temperature for 5 to 8 hours. The resulting solid was filtered and washed with cooled methanol, the resulting solution was concentrated, and the residue was purified through a silica gel column to prepare the target compound.

[Compound No. 1]

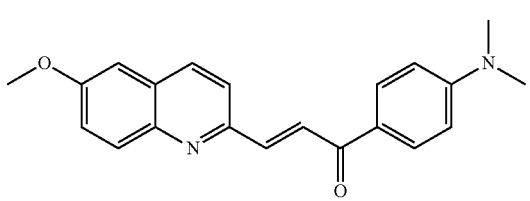

Yellow solid, yield 89%. $^1$H NMR (400 MHz, CDCl$_3$, 25° C., TMS) δ 8.19 (d, J=15.6 Hz, 1H), 8.12 (d, J=8.8 Hz, 1H), 8.08 (d, J=9.2 Hz, 1H), 8.06 (d, J=8.8 Hz, 2H), 7.93 (d, J=15.6 Hz, 1H), 7.63 (d, J=8.4 Hz, 1H), 7.41 (dd, J=2.8 Hz, J=9.2 Hz, 1H), 7.09 (d, J=2.8 Hz, 1H), 6.74 (d, J=8.8 Hz, 2H), 3.97 (S, 3H, OCH$_3$), 3.11 (s, 6H, N(CH$_3$)$_2$).

Example 2

(E)-1-(4-(tert-butoxycarboxamino)phenyl)-3-(6-methoxyquinolin-2-yl)prop-2-en-1-one (Compound 13b) [Compound No. 2]

[Compound No. 2]

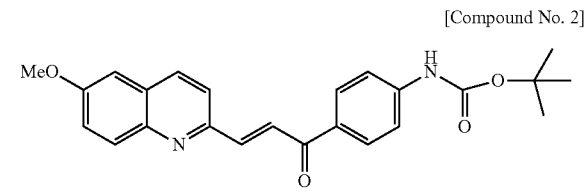

White solid, yield 82%. $^1$H NMR (400 MHz, CDCl$_3$, 25° C., TMS) b 8.15 (d, J=16.0 Hz, 1H), 8.13 (d, J=8.4 Hz, 2H), 8.12 (d, J=9.6 Hz, 1H), 8.07 (d, J=9.2 Hz, 1H), 7.95 (d, J=15.2 Hz, 1H), 7.65 (d, J=8.4 Hz, 1H), 7.54 (d, J=8.8 Hz, 2H), 7.43 (dd, J=2.6 Hz, J=9.2 Hz, 1H), 7.11 (d, J=2.8 Hz, 1H), 6.74 (brs, 1H, NH), 3.98 (S, 3H, OCH$_3$), 1.60 (s, 9H).

Example 3: (E)-1-(4-tolyl)-3-(6-methoxyquinolin-2-yl)prop-2-en-1-one (Compound 13d) [Compound No. 4]

[Compound No. 4]

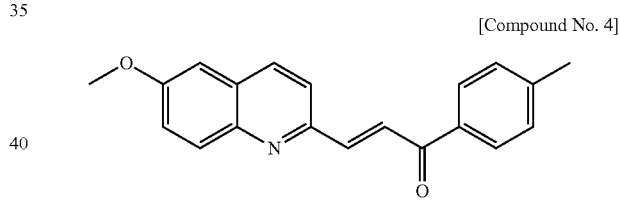

White solid, yield 76%. $^1$H NMR (400 MHz, CDCl$_3$, 25° C., TMS) δ 8.13 (d, J=15.2 Hz, 1H), 8.08 (d, J=9.2 Hz, 1H), 8.07-8.04 (m, 3H), 7.95 (d, J=15.6 Hz, 1H), 7.65 (d, J=8.4 Hz, 1H), 7.43 (dd, J=2.8 Hz, J=9.2 Hz, 1H), 7.35 (d, J=8.0, 2H), 7.10 (d, J=2.8 Hz, 1H), 3.98 (S, 3H, OCH$_3$), 2.47 (s, 3H, CH$_3$).

Example 4

(E)-1-(4-bromophenyl)-3-(6-methoxyquinolin-2-yl)prop-2-en-1-one (Compound 13e) [Compound No. 5]

[Compound No. 5]

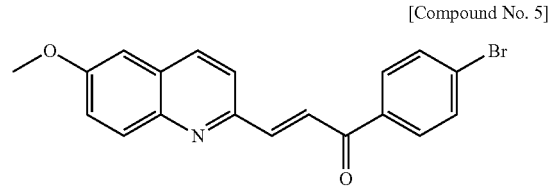

White solid, yield 72%. $^1$H NMR (400 MHz, CDCl$_3$, 25° C., TMS) δ 8.12 (d, J=8.4 Hz, 1H), 8.10 (d, J=15.6 Hz, 1H), 8.06 (d, J=9.2 Hz, 1H), 8.01 (d, J=8.4 Hz, 2H), 7.96 (d, J=15.2 Hz, 1H), 7.70 (d, J=8.4 Hz, 2H), 7.44 (d, J=8.4 Hz, 1H), 7.35 (dd, J=2.6 Hz, J=9.2 Hz, 1H), 7.11 (d, J=2.4 Hz, 1H), 3.98 (s, 3H, OCH$_3$).

Example 5

(E)-1-(4-aminophenyl)-3-(6-hydroxyquinolin-2-yl)prop-2-en-1-one (Compound 13c) [Compound No. 3]

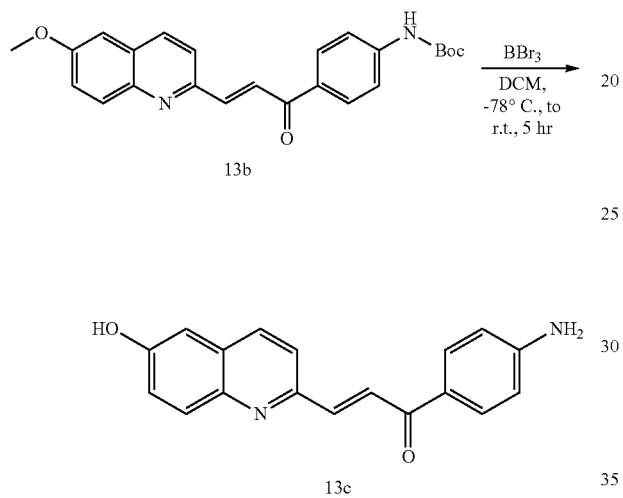

Compound 13b (400 mg, 1.0 mmol) was dissolved in anhydrous dichloromethane (5 mL), and boron tribromide (BBr$_3$; 1.0 M dichloromethane (DCM), 2 mL, 2.0 mmol) was added dropwise at −78° C. in a nitrogen atmosphere. The reaction solution was stirred at room temperature for 5 hours, neutralized in 2N NaOH, and extracted 3 times with chloroform and methanol (10:1). The organic layer was dried with sodium sulfate (Na$_2$SO$_4$), the solvent was concentrated under reduced pressure, and the residue was purified by silica gel column chromatography (dichloromethane/methanol=98:2) to prepare a yellow solid Compound 13c (180 mg, 63%).

[Compound No. 3]

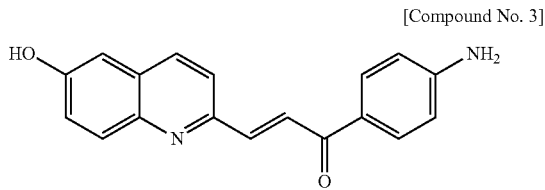

$^1$H NMR (400 MHz, DMSO-d$_6$, 25° C., TMS) δ 10.22 (S, 1H, OH), 8.21 (d, J=8.4 Hz, 1H), 8.17 (d, J=15.6 Hz, 1H), 8.05 (d, J=8.4 Hz, 1H), 7.94 (d, J=8.8 Hz, $^1$H), 7.92 (d, J=9.2 Hz, 1H), 7.70 (d, J=15.6 Hz, 1H), 7.35 (dd, J=2.4 Hz, J=9.2 Hz, 1H), 7.18 (d, J=2.4 Hz, 1H), 6.65 (d, J=8.4 Hz, 2H), 6.23 (s, 2H, NH$_2$).

Example 6: (E)-6-methoxy-2-(4-(trifluoromethyl)styryl)quinolone (Compound 14a) [Compound No. 6]

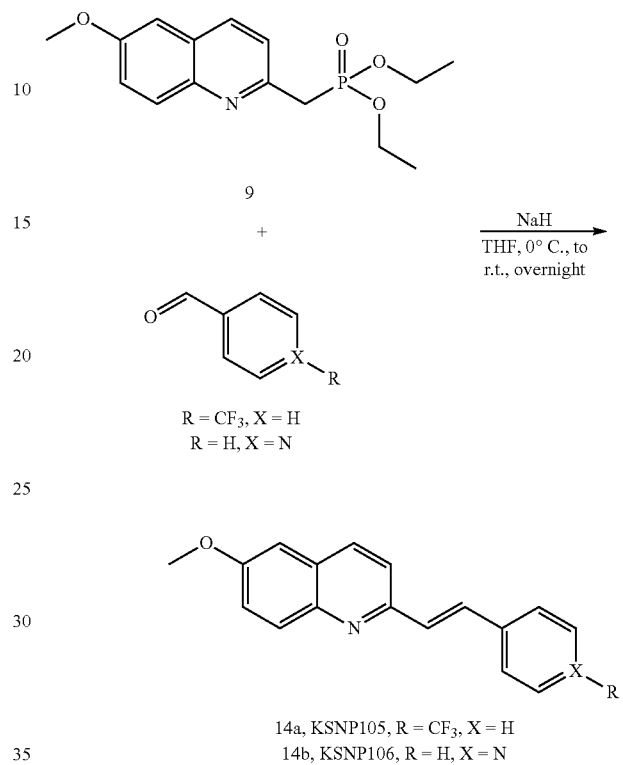

Compound 9 (1.20 mmol), prepared by the method of Reference Example 8, was dissolved in THF, NaH (2.0 mmol) was added thereto under a nitrogen atmosphere, and fluorophenyl aldehyde (1.0 mmol) was added dropwise at 0° C. Then, the mixture was stirred at room temperature for 18 hours. The reaction solution was poured into 20 mL water and extracted with ethyl acetate. The organic layer was washed with brine and dried over sodium sulfate (Na$_2$SO$_4$). Then, the solvent was concentrated under reduced pressure and purified through silica gel column chromatography to prepare the target compound.

[Compound No. 6]

White solid, yield 54%. $^1$H NMR (400 MHz, CDCl$_3$, 25° C., TMS) δ 8.07 (d, J=8.8 Hz, 1H), 8.01 (d, J=9.2 Hz, 1H), 7.74 (d, J=8.4 Hz, 2H), 7.68 (d, J=15.6 Hz, 1H), 7.67 (d, J=8.4 Hz, 2H), 7.65 (d, J=8.0 Hz, 1H), 7.46 (d, J=16.0 Hz, 1H), 7.41 (dd, J=2.8 Hz, J=9.2 Hz, 1H), 7.10 (d, J=2.8 Hz, 1H), 3.98 (s, 3H, OCH$_3$).

Example 7: (E)-6-methoxy-2-(2-(pyridin-4-yl)vinyl) quinolone (Compound 14b) [Compound No. 7]

[Compound No. 7]

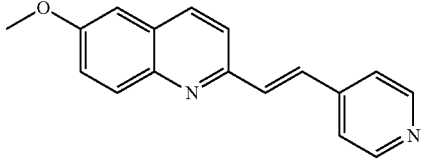

White solid, yield 61%. $^1$H NMR (400 MHz, CDCl$_3$, 25° C., TMS) δ 8.62 (d, J=4.4 Hz, 2H), 8.07 (d, J=8.4 Hz, 1H), 8.00 (d, J=9.2 Hz, 1H), 7.63 (d, J=8.4 Hz, 1H), 7.57 (d, J=16.4 Hz, 1H), 7.52 (d, J=16.0 Hz, 1H), 7.47 (d, J=4.8 Hz, 2H), 7.40 (dd, J=2.8 Hz, J=9.2 Hz, 1H), 7.08 (d, J=2.8 Hz, 1H), 3.95 (s, 3H, OCH$_3$).

Example 8

Tert-butyl(4-((1E,3E)-4-(6-methoxyquinolin-2-yl) buta-1,3-dien-1-yl)phenyl)(methyl)carbamate (Compound 15a)

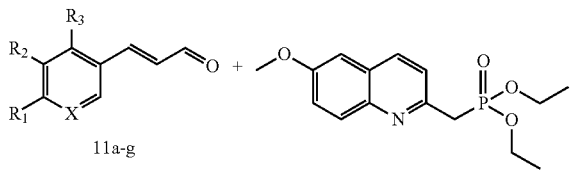

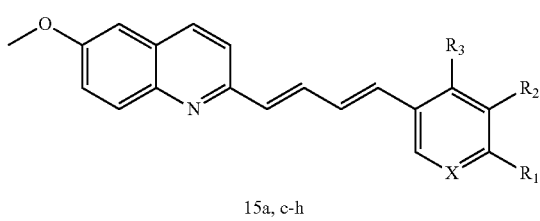

Compounds 15a, 15c to 15h were prepared by synthesis in the same manner as in Example 6.

Yellow solid, yield 73%. $^1$H NMR (400 MHz, CDCl$_3$, 25° C., TMS) δ 7.98 (d, J=8.8 Hz, 1H), 7.95 (d, J=9.2 Hz, 1H), 7.53 (d, J=8.8 Hz, 1H), 7.46 (d, J=15.2 Hz, 1H), 7.43 (d, J=8.4 Hz, 2H), 7.35 (dd, J=2.8 Hz, J=9.2 Hz, 1H), 7.22 (d, J=8.4 Hz, 2H), 7.04 (d, J=2.8 Hz, 1H), 7.01 (d, J=15.6 Hz, 1H), 6.91 (d, J=15.6 Hz, 1H), 6.80 (d, J=15.6 Hz, 1H), 3.93 (s, 3H, OCH$_3$), 3.27 (s, 3H, CH$_3$), 1.47 (s, 9H).

Example 9

6-methoxy-2-((1E,3E)-4-(3-chlorophenyl)buta-1,3-dien-1-yl)quinolone (Compound 15f) [Compound No. 8]

[Compound No. 8]

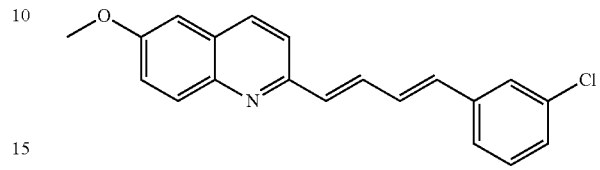

White solid, yield 61%. $^1$H NMR (400 MHz, CDCl$_3$, 25° C., TMS) b 8.00 (d, J=8.8 Hz, 1H), 7.95 (d, J=9.2 Hz, 1H), 7.53 (d, J=8.4 Hz, 1H), 7.48-7.41 (m, 2H), 7.35 (dd, J=2.8 Hz, J=9.2 Hz, 1H), 7.32 (d, J=15.6 Hz, 1H), 7.30-7.23 (m, 1H), 7.050 (d, J=15.6 Hz, 1H), 7.049 (d, J=2.8 Hz, 1H), 6.94 (d, J=15.6 Hz, 1H), 6.75 (d, J=15.6 Hz, 1H), 3.94 (s, 3H, OCH$_3$).

Example 10

6-methoxy-2-((1E,3E)-4-(3-nitrophenyl)buta-1,3-dien-1-yl)quinolone (Compound 15g) [Compound No. 9]

[Compound No. 9]

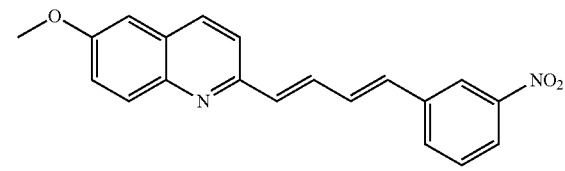

Yellow solid, yield 65%. $^1$H NMR (400 MHz, CDCl$_3$, 25° C., TMS) δ 8.30 (d, J=1.6 Hz, 1H), 8.09 (dd, J=1.4 Hz, J=8.0 Hz, 1H), 8.01 (d, J=8.4 Hz, 1H), 7.96 (d, J=9.2 Hz, 1H), 7.76 (d, J=7.6 Hz, 1H), 7.54-7.51 (m, 2H), 7.47 (d, J=15.6 Hz, 1H), 7.35 (dd, J=2.8 Hz, J=9.2 Hz, 1H), 7.14 (d, J=15.6 Hz, 1H), 7.05 (d, J=2.8 Hz, 1H), 7.00 (d, J=15.6 Hz, 1H), 6.84 (d, J=15.6 Hz, 1H), 3.94 (s, 3H, OCH$_3$).

Example 11

6-methoxy-2-((1E,3E)-4-(2,4-difluorophenyl)buta-1,3-dien-1-yl)quinolone (Compound 15h) [Compound No. 10]

[Compound No. 10]

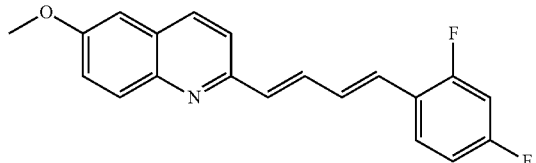

White solid, yield 54%. $^1$H NMR (400 MHz, CDCl$_3$, 25° C., TMS) δ 7.99 (d, J=8.4 Hz, 1H), 7.95 (d, J=9.2 Hz, 1H), 7.55 (d, J=8.0 Hz, 1H), 7.50-7.45 (m, 1H), 7.43 (d, J=15.2 Hz, 1H), 7.35 (dd, J=2.8 Hz, J=9.2 Hz, 1H), 7.05 (d, J=15.6 Hz, 1H), 7.03 (d, J=15.2 Hz, 1H), 6.95-6.90 (m, 2H), 6.84 (d, J=15.6 Hz, 1H), 6.82-6.80 (m, 1H), 3.93 (s, 3H, OCH$_3$).

Example 12

4-((1E,3E)-4-(6-methoxyquinolin-2-yl)buta-1,3-dien-1-yl)-N-methylanaline (Compound 15b) [Compound No. 11]

Compound 15a (70 mg, 0.17 mmol), prepared in Example 8, was dissolved in dichloromethane (3 mL), trifluoroacetic acid (96 mg, 0.84 mmol) was added to the resulting solution at 0° C., and the mixture was stirred at room temperature for 3 hours. Then, the reaction solution was carefully neutralized (pH 7-8) with a sodium hydrogen carbonate (NaHCO$_3$) solution. The reaction mixture was extracted with dichloromethane, and the organic layer was dried over sodium sulfate (Na$_2$SO$_4$). Then, the solvent was concentrated under reduced pressure and purified through silica gel column chromatography (hexane/ethyl acetate=1:1) to prepare a target Compound 15b (33 mg, 62%) having no tertiary butyl carboxyl group as a white solid.

[Compound No. 11]

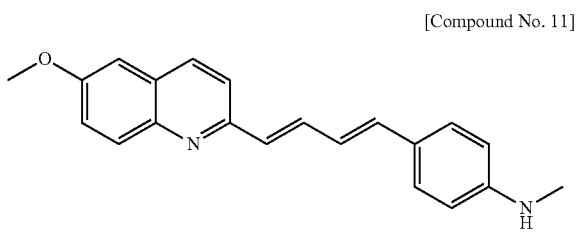

$^1$H NMR (400 MHz, CDCl$_3$, 25° C., TMS) δ 7.94 (d, J=8.8 Hz, 1H), 7.93 (d, J=9.2 Hz, 1H), 7.52 (d, J=8.4 Hz, 1H), 7.44 (d, J=15.6 Hz, 1H), 7.34 (d, J=8.8 Hz, 2H), 7.33 (dd, J=2.6 Hz, J=9.2 Hz, 1H), 7.04 (d, J=2.8 Hz, 1H), 7.03 (d, J=15.2 Hz, 1H), 6.85 (d, J=15.6 Hz, 1H), 6.82 (d, J=15.6 Hz, 1H), 6.59 (d, J=8.4 Hz, 2H), 3.93 (s, 3H, OCH$_3$), 2.87 (s, 3H, CH$_3$).

Example 13

6-methoxy-2-((1E,3E)-4-(6-nitropyridin-3-yl)buta-1,3-dien-1-yl)quinolone (Compound 15e) [Compound No. 12]

[Compound No. 12]

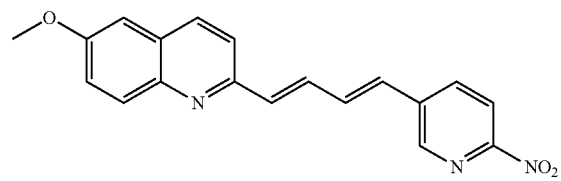

Yellow solid, yield 53%. $^1$H NMR (400 MHz, CDCl$_3$, 25° C., TMS) δ 8.67 (d, J=0.8 Hz, 1H), 8.26 (d, J=8.4 Hz, 1H), 8.07 (dd, J=1.2 Hz, J=8.4 Hz, 1H), 8.04 (d, J=8.8 Hz, 1H), 7.97 (d, J=9.2 Hz, 1H), 7.54 (d, J=8.8 Hz, 1H), 7.52 (d, J=15.2 Hz, 1H), 7.38 (dd, J=2.4 Hz, J=9.2 Hz, 1H), 7.23 (d, J=2.8 Hz, 1H), 7.08 (d, J=15.2 Hz, 1H), 7.04 (d, J=15.6 Hz, 1H), 6.87 (d, J=15.6 Hz, 1H), 3.95 (s, 3H, OCH$_3$).

Example 14

4-((1E,3E)-4-(6-methoxyquinolin-2-yl)buta-1,3-dien-1-yl)-N,N-dimethylaniline (Compound 15c) [Compound No. 13]

[Compound No. 13]

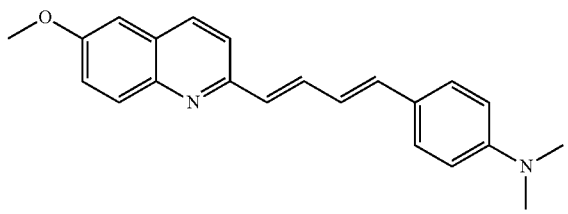

Red solid, yield 71%. $^1$H NMR (400 MHz, CDCl$_3$, 25° C., TMS) b 7.95 (d, J=8.4 Hz, 1H), 7.93 (d, J=8.8 Hz, 1H), 7.52 (d, J=8.8 Hz, 1H), 7.44 (d, J=15.6 Hz, 1H), 7.38 (d, J=8.8 Hz, 2H), 7.34 (dd, J=2.4 Hz, J=9.2 Hz, 1H), 7.03 (d, J=2.8 Hz, 1H), 6.89 (d, J=15.2 Hz, 1H), 6.82 (d, J=15.6 Hz, 1H), 6.76 (d, J=15.2 Hz, 1H), 6.70 (d, J=8.8 Hz, 2H), 3.92 (s, 3H, OCH$_3$), 2.99 (s, 6H, N(CH$_3$)$_2$).

Example 15

5-((1E,3E)-4-(6-methoxyquinolin-2-yl)buta-1,3-dien-1-yl)-N,N-dimethylpyridin-2-amine (Compound 15d) [Compound No. 14]

[Compound No. 14]

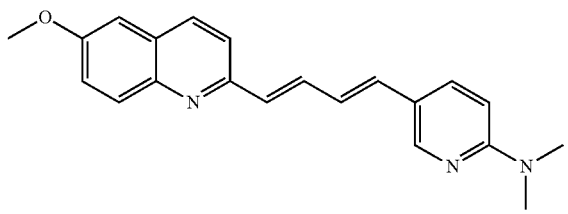

Yellow solid, yield 68%. $^1$H NMR (400 MHz, CDCl$_3$, 25° C., TMS) δ 8.21 (d, J=2.0 Hz, 1H), 7.96 (d, J=8.8 Hz, 1H), 7.93 (d, J=9.2 Hz, 1H), 7.66 (dd, J=2.4 Hz, J=8.8 Hz, 1H), 7.52 (d, J=8.4 Hz, 1H), 7.43 (d, J=15.6 Hz, 1H), 7.33 (dd, J=2.8 Hz, J=8.8 Hz, 1H), 7.03 (d, J=2.8 Hz, 1H), 6.86 (d, J=15.2 Hz, 1H), 6.83 (d, J=15.6 Hz, 1H), 6.72 (d, J=15.6 Hz, 1H), 6.53 (d, J=8.8 Hz, 1H), 3.93 (s, 3H, OCH$_3$), 3.13 (s, 6H, N(CH$_3$)$_2$).

Example 16

Tert-butyl(44(1E,3E)-5-(6-methoxyquinolin-2-yl)-5-oxopenta-1,3-dien-1-yl)phenyl) (methyl)carbamate (Compound 16a)

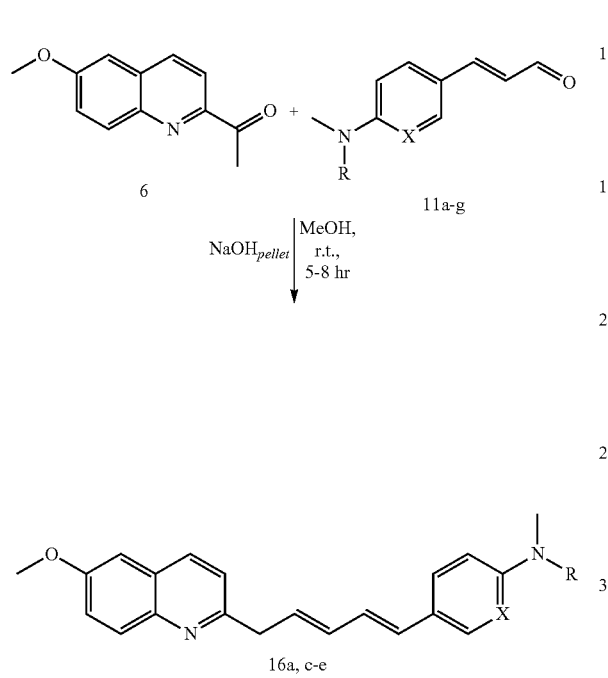

Compounds 16a, 16c to 16e were prepared using the same preparation method as in Example 1.

Example 17

(2E,4E)-5-(4-(dimethylamino)phenyl)-1-(6-methoxyquinolin-2-yl)penta-2,4-dien-1-one (Compound 16c) [Compound No. 15]

[Compound No. 15]

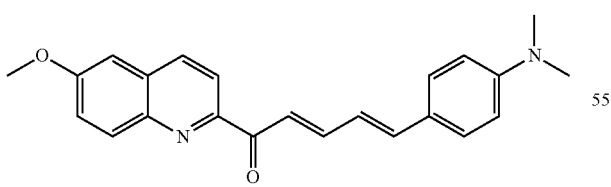

Red powder, yield 84%. $^1$H NMR (400 MHz, CDCl$_3$, 25° C., TMS) b 8.23 (d, J=8.8 Hz, 1H), 8.16 (d, J=8.8 Hz, 1H), 8.12 (d, J=9.2 Hz, 1H), 7.95 (d, J=15.2 Hz, 1H), 7.82-7.76 (m, 1H), 7.433 (d, J=8.8 Hz, 2H), 7.429 (dd, J=3 Hz, J=8.8 Hz, 1H), 7.12 (d, J=2.8 Hz, 1H), 7.02 (d, J=15.2 Hz, 1H), 6.98 (d, J=15.2 Hz, 1H), 6.70 (d, J=8.8 Hz, 2H), 3.97 (s, 3H, OCH$_3$), 3.03 (s, 6H, N(CH$_3$)$_2$).

Example 18

(2E,4E)-5-(6-(dimethylamino)pyridin-3-yl)-1-(6-methoxyquinolin-2-yl)penta-2,4-dien-1-one (Compound 16d) [Compound No. 16]

[Compound No. 16]

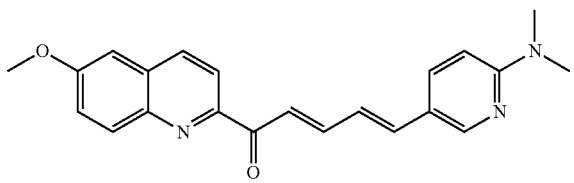

Yellow powder, yield 71%. $^1$H NMR (400 MHz, CDCl$_3$, 25° C., TMS) δ 8.27 (d, J=2.4 Hz, 1H), 8.23 (d, J=8.4 Hz, 1H), 8.16 (d, J=8.8 Hz, 1H), 8.12 (d, J=9.2 Hz, 1H), 7.96 (d, J=15.2 Hz, 1H), 7.80-7.74 (m, 1H), 7.69 (dd, J=2.4 Hz, J=8.8 Hz, 1H), 7.43 (dd, J=2.8 Hz, J=9.2 Hz, 1H), 7.13 (d, J=2.8 Hz, 1H), 6.97 (d, J=15.6 Hz, 1H), 6.95 (d, J=15.6 Hz, 1H), 6.55 (d, J=8.8 Hz, 2H), 3.97 (s, 3H, OCH$_3$), 3.15 (s, 6H, N(CH$_3$)$_2$).

Example 19

(2E,4E)-1-(6-methoxyquinolin-2-yl)-5-(4-(methylamino)phenyl)penta-2,4-dien-1-one (Compound 16b) [Compound No. 17]

[Compound No. 17]

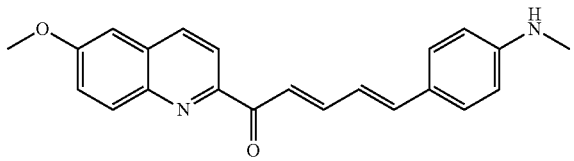

Compound 16a was synthesized in the same preparation process as in Example 12 above.

Red solid, yield 73%. $^1$H NMR (400 MHz, CDCl$_3$, 25° C., TMS) δ 8.56 (d, J=8.8 Hz, 1H), 8.33 (d, J=16 Hz, 1H), 7.79 (d, J=16.0 Hz, 1H), 7.42 (d, J=8.4 Hz, 1H), 7.41-7.38 (m, 3H), 7.37-7.33 (m, 3H), 7.07 (d, J=15.2 Hz, 1H), 7.05 (d, J=15.2 Hz, 1H), 6.63 (d, J=8.4 Hz, 2H), 3.99 (s, 3H, OCH$_3$), 2.89 (s, 3H, CH$_3$).

Example 20

(2E,4E)-5-(44(2-hydroxyethyl)(methyl)amino)phenyl)-1-(6-methoxyquinolin-2-yl) penta-2,4-dien-1-one (Compound 16e) [Compound No. 18]

[Compound No. 18]

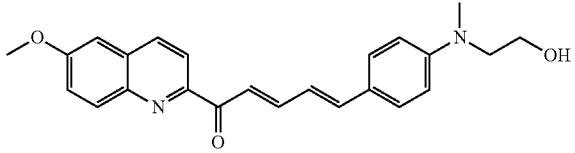 [SMILES: COc1ccc2nc(C(=O)/C=C/C=C/c3ccc(N(C)CCO)cc3)ccc2c1]

Red solid, yield 61%. $^1$H NMR (400 MHz, CDCl$_3$, 25° C., TMS) δ 8.62 (d, J=8.8 Hz, 1H), 8.29 (d, J=8.8 Hz, 1H), 8.19 (d, J=9.2 Hz, 1H), 7.91 (d, J=15.2 Hz, 1H), 7.81-7.77 (m, 1H), 7.59 (d, J=9.6 Hz, 1H), 7.41 (d, J=8.8 Hz, 2H), 7.39-7.33 (m, 1H), 7.01 (d, J=15.2 Hz, 1H), 6.98 (d, J=15.2 Hz, 1H), 6.74 (d, J=8.8 Hz, 2H), 4.10 (s, 3H, OCH$_3$), 3.86 (t, J=5.4 Hz, 2H), 3.57 (t, J=5.4 Hz, 2H), 1.80 (t, J=5.4 Hz, 1H, OH).

Experimental Example 1: Measurement of Fluorescence of Synthesized Compound

In order to investigate the optical properties of the newly synthesized compound in the present invention, the absorbance was measured using a V-730 UV-visible spectrophotometer manufactured by JASCO, and fluorescence was measured using a FlexStation 3 multi-mode microplate reader manufactured by Molecular Devices. Absorbance and fluorescence were measured three times at a concentration of 10 μM in ethanol, and the average thereof is shown in Table 1 below. At this time, T807 (AV-1451) as a Tau positron-emission-tomography (PET) tracer and Thioflavin S, which are commercially available to detect tau production in vivo, were used as a control group.

As a result of absorbance and fluorescence measurements, the newly synthesized compound in the present invention was found to be capable of emitting light at a fluorescence wavelength of 500 nm to 710 nm and to have a high Stokes shift of 90 nm to 220 nm. The measurement results are shown in Table 1 below.

TABLE 1

Results of synthetic compound fluorescence measurement

| Compound | $\lambda_{ex}^a$ | $\lambda_{em}^b$ | Stokes shift | clogP$^c$ |
|---|---|---|---|---|
| Thioflavin S | 347 nm | 451 nm | 104 nm | — |
| T807 (AV-1451) | 304 nm | 369 nm | 65 nm | 3.18 |
| 13a (Compound No. 1) | 339 nm | 601 nm | 202 nm | 4.28 |
| 13c (Compound No. 3) | 378 nm | 570 nm | 192 nm | 2.84 |
| 13d (Compound No. 4) | 314 nm | 454 nm | 140 nm | 4.30 |
| 13e (Compound No. 5) | 314 nm | 415 nm | 101 nm | 4.74 |
| 14a (Compound No. 6) | 359 nm | 415 nm | 56 nm | 5.90 |
| 14b (Compound No. 7) | 357 nm | 420 nm | 63 nm | 3.52 |
| 15f (Compound No. 8) | 360 nm | 415 nm | 55 nm | 5.93 |
| 15g (Compound No. 9) | 361 nm | 452 nm | 91 nm | 4.96 |
| 15h (Compound No. 10) | 360 nm | 415 nm | 55 nm | 5.51 |
| 15b (Compound No. 11) | 400 nm | 602 nm | 202 nm | 4.72 |
| 15e (Compound No. 12) | 389 nm | 587 nm | 198 nm | 3.65 |
| 15c (Compound No. 13) | 399 nm | 600 nm | 201 nm | 5.38 |
| 15d (Compound No. 14) | 402 nm | 520 nm | 118 nm | 4.44 |
| 16c (Compound No. 15) | 450 nm | 678 nm | 228 nm | 5.16 |
| 16d (Compound No. 16) | 425 nm | 637 nm | 212 nm | 4.21 |
| 16b (Compound No. 17) | 475 nm | 714 nm | 239 nm | 4.42 |
| 16e (Compound No. 18) | 436 nm | 658 nm | 222 nm | 4.49 |

$\lambda_{ex}^a$: Maximum excitation wavelength
$\lambda_{em}^b$: Maximum emission wavelength
Stokes shift: Difference between excitation energy and emission energy in accordance with Stokes' law
clogP$^c$: a distribution coefficient of the compound and is a measure of lipophilicity

Experimental Example 2: Binding Assay of Tau Aggregates and Amyloid Beta Aggregates of Synthetic Compounds In Vitro Experimental Example 2-1: Tau and amyloid beta aggregation induction For amyloid aggregation induction, the synthesized Abeta40 (Amyloid Beta 40) peptide was dissolved in PBS at a concentration of 0.5 mg/ml to induce aggregation for 7 days at 37° C. and 200 rpm with shaking. To induce aggregation of tau proteins, aggregation of Tau-K18 protein (0.5 mg/ml in PBS) purified and isolated from E. coli with heparin (0.1 mg/ml) and DTT (100 μM) was induced at 37° C. and 200 rpm for 7 days under shaking conditions.

Experimental Example 2-2: Measurement of Labeling Ability of Tau and Amyloid Aggregate Derivatives Since aggregation of tau and amyloid occurs only in a pathological environment, the reactivity of tau proteins (pre-aggregates) that do not aggregate with synthetic products and tau proteins (aggregates) that aggregate with synthetic products was compared and analyzed to determine whether or not the newly synthesized compound is capable of labeling tau aggregate proteins. At this time, thioflavin S (Th S), which is known to bind to beta-sheet structures such as tau and amyloid aggregates, was used as a control group (Ex: 430 nm, Em: 480-610 nm). Specifically, in order to determine the labeling ability of newly synthesized compounds to tau aggregate proteins, a 25 μl dilution of a 10 μM labeling substance in PBS and 25 id of a 0.125 mg/ml tau or amyloid pre-aggregate or aggregate diluted in PBS were each incubated for 30 minutes, and then a fluorescence spectrum reaction was measured using a spectrophotometer. Here, the excitation (Ex) wavelength and the emission (Em) wavelength for each compound are shown in Table 2 below.

Experimental Example 2-3: Measurement of non-specific binding using BSA

In order to exclude non-specific binding of the compound to serum, reactivity between the compound and bovine serum albumin (BSA) was further tested. 25 μl of a 10 μM compound was incubated along with 25 μl of 0.25 mg/ml BSA for 30 minutes, and then the fluorescence spectrum reaction was measured using a spectrophotometer. At this time, the excitation (Ex) wavelength and the emission (Em) wavelength for each compound are shown in Table 2 below. The BSA response was conducted to identify non-selective binding to other proteins in the blood when applied to patients as an imaging agent.

Figure 1B:
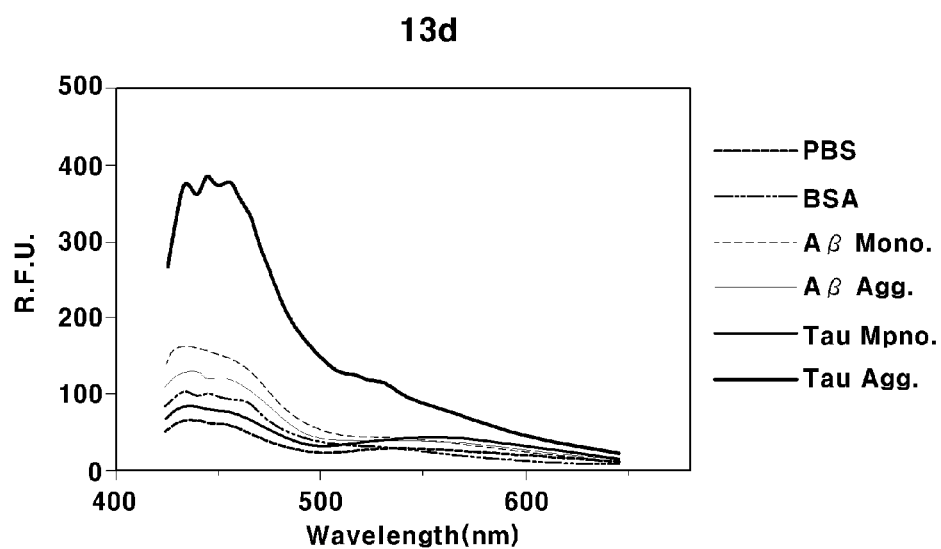
Figure 1C:
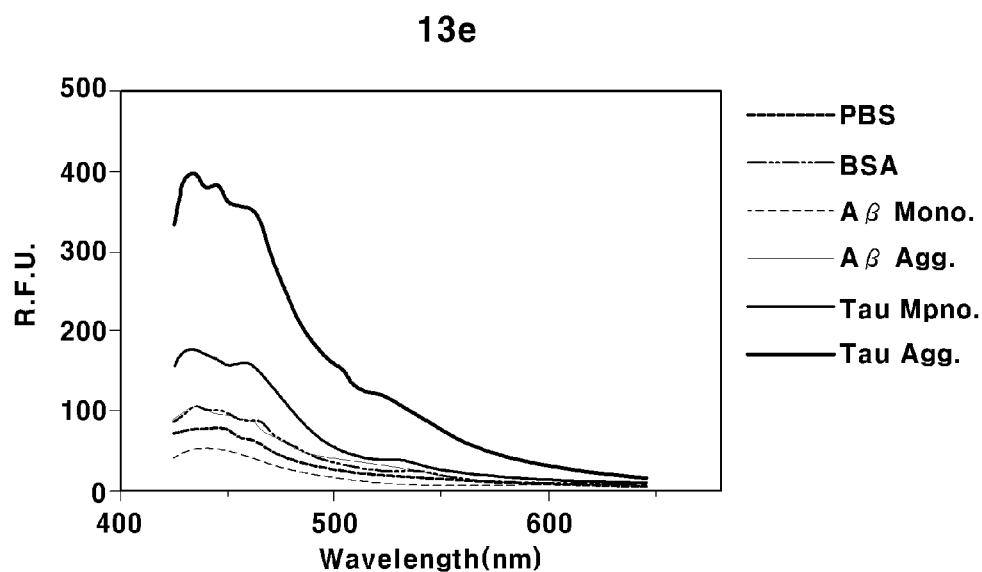
Figure 1D:
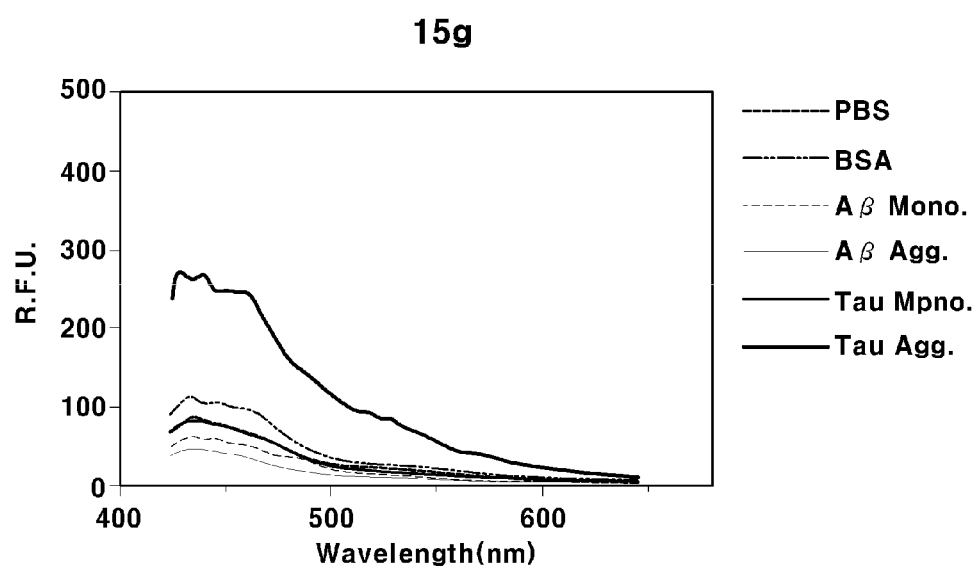
Figure 1E:
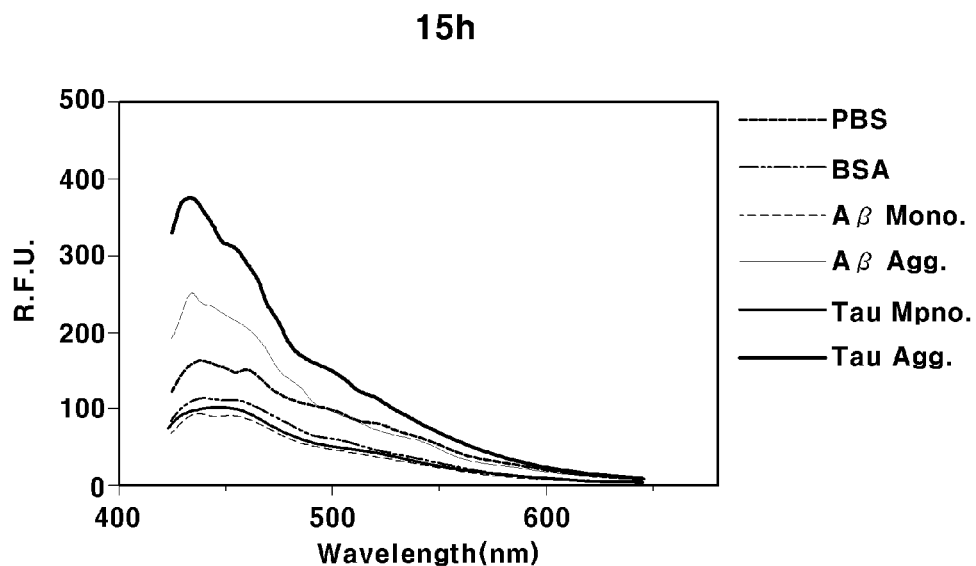
Figure 1F:
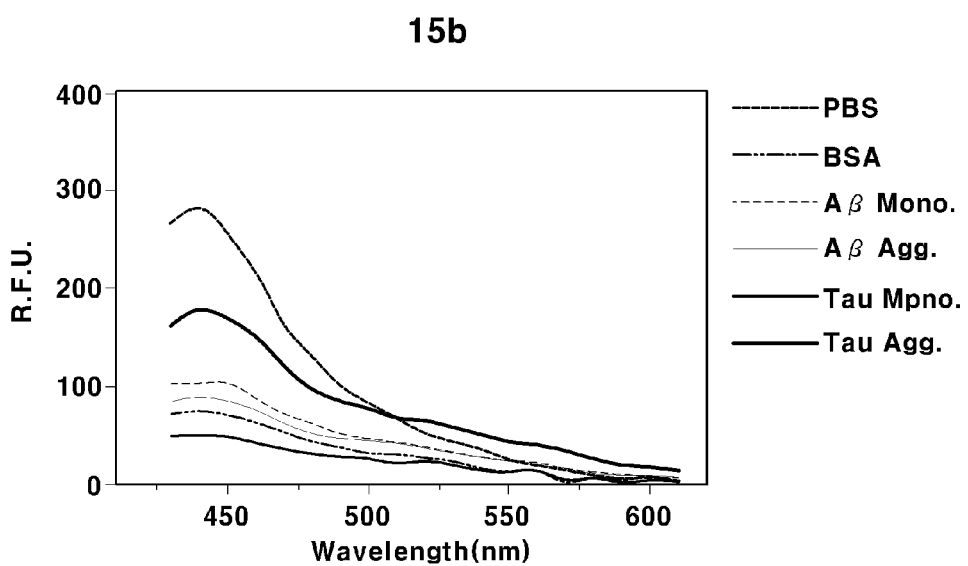
Figure 1G:
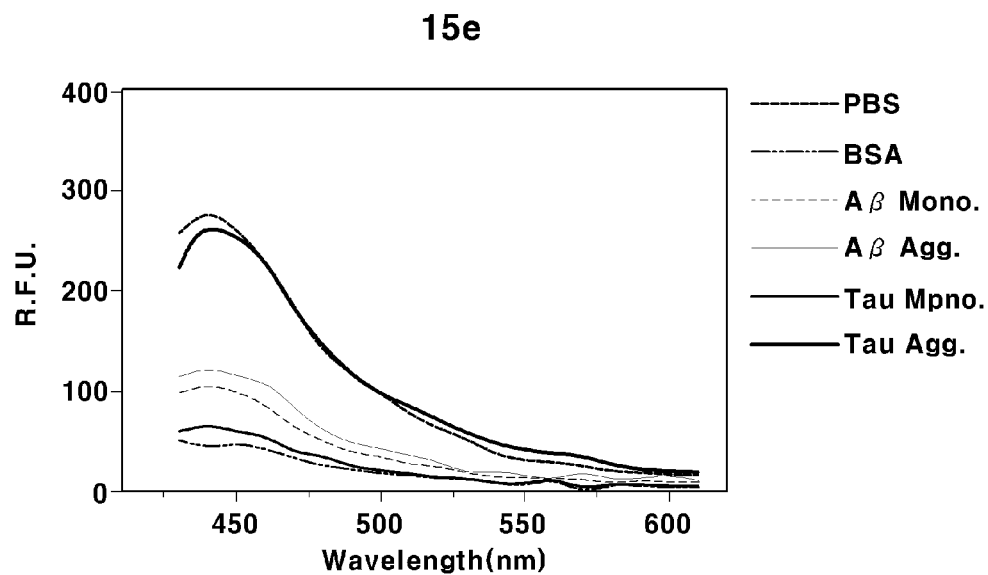
Figure 1H:
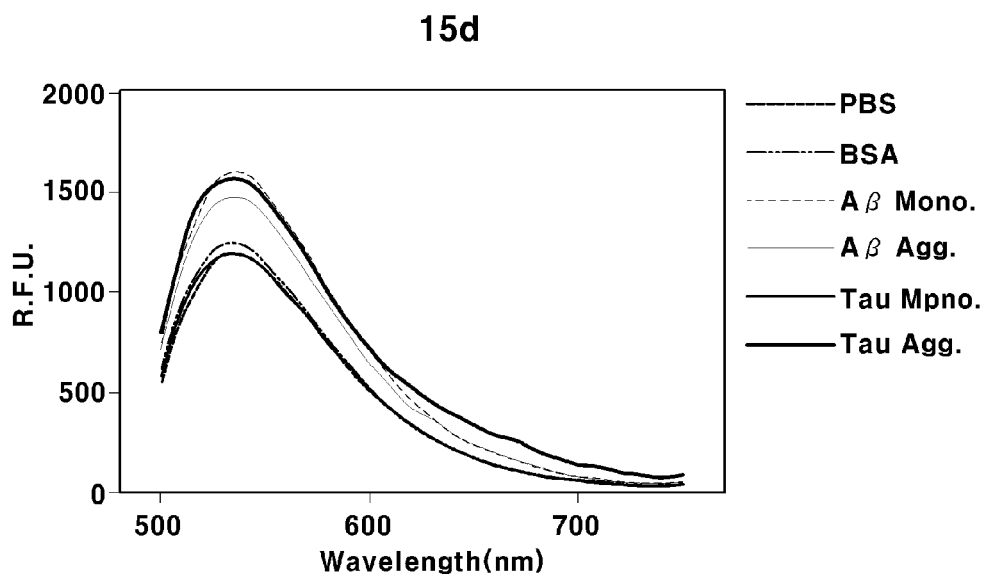
Figure 1I:
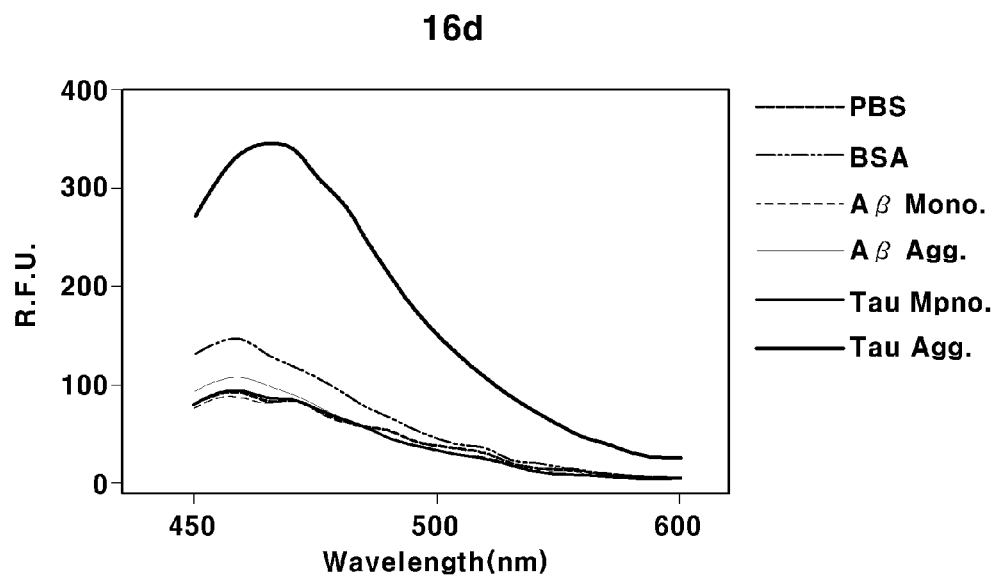
Figure 1J:
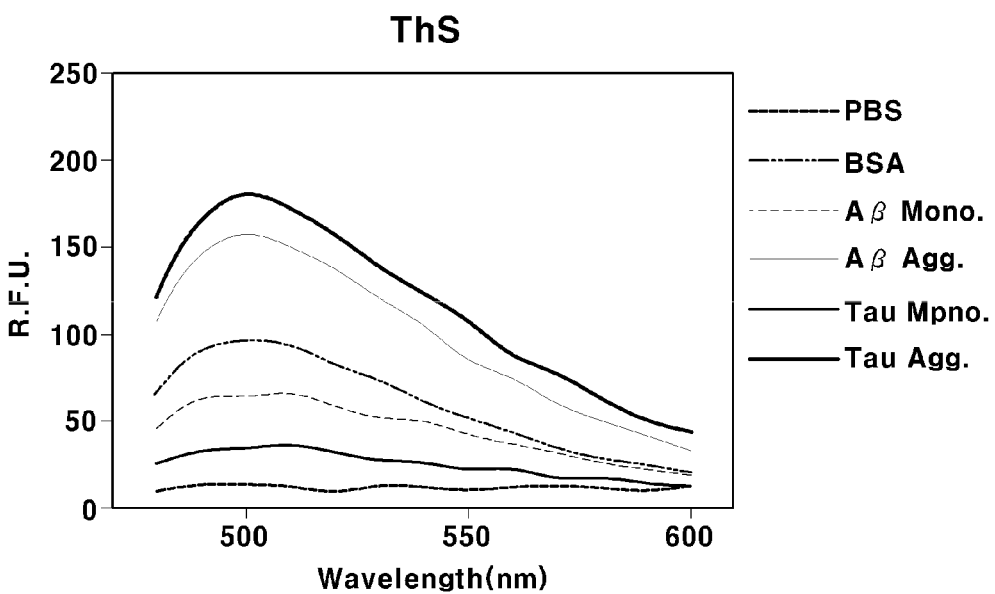

Selectivity analysis for tau aggregates and amyloid beta aggregates of the novel synthetic compounds of the present invention was performed as described above, and the resulting in vitro fluorescence changes are summarized in Table 2 and FIG. 1 below.

As the results of screening the novel synthetic compounds of the present invention as fluorescent probes in vitro with regard to the tau/amyloid beta labeling ability, probe 13a ((E)-1-(4-(dimethylamino)phenyl)-3-(6-methoxyquinolin-2-yl)prop-2-en-1-one), 13e ((E)-1-(4-(bromophenyl)-3-(6-methoxyquinolin-2-yl)prop-2-en-1-one), 15g (6-methoxy-2-((1E,3E)-4-(3-nitrophenyl)buta-1,3-dien-1-yl)quinolone), 16d ((2E,4E)-5-(6-(dimethylamino)pyridin-3-yl)-1-(6-methoxyquinolin-2-yl)penta-2,4-dien-1-one) were found to have higher selectivity for tau aggregates than for amyloid aggregates, and 13a, 13e, 15g and 16d had 4.6 times, 3.8 times, 5.8 times and 3.5 times the selectivity, respectively. Thioflavin S exhibited high reactivity to BSA, whereas the screened compound exhibited relatively low reactivity to BSA, except probe 16b.

[Table 2]

Measurement results of fluorescence changes of synthesized near-infrared probes according to binding to tau aggregates, amyloid beta aggregates and bovine serum albumin (BSA).

| Compound (10 μM) | Ex (nm) | Em (nm) | FI$^a$ $FI_{tau}$ | $FI_{A\beta}$ | $FI_{BSA}$ | SI$^b$ $SI_{a\beta}$ | $SI_{tau/mono}$ |
|---|---|---|---|---|---|---|---|
| Thioflavin S | 430 | 500 | 15.32 | 19.95 | 7.133 | 0.8 | 4.3 |
| 13a (Compound No. 1) | 310 | 440 | 5.12 | 1.10 | 1.23 | 4.6 | 5.2 |
| 13c (Compound No. 3) | 310 | 435 | 4.63 | 1.67 | 1.72 | 2.8 | 3.2 |
| 13d (Compound No. 4) | 310 | 445 | 6.05 | 1.88 | 1.57 | 3.2 | 4.8 |
| 13e (Compound No. 5) | 310 | 435 | 5.18 | 1.37 | 1.39 | 3.8 | 2.2 |
| 14a (Compound No. 6) | 310 | 455 | 1.01 | 0.54 | 0.60 | 1.9 | 2.0 |
| 14b (Compound No. 7) | 310 | 455 | 0.79 | 0.57 | 0.61 | 1.4 | 1.3 |
| 15f (Compound No. 8) | 310 | 435 | 3.91 | 3.27 | 1.75 | 1.2 | 4.4 |
| 15g (Compound No. 9) | 310 | 430 | 3.42 | 0.58 | 1.33 | 5.8 | 3.7 |
| 15h (Compound No. 10) | 310 | 435 | 2.35 | 1.56 | 0.70 | 1.5 | 2.8 |
| 15b (Compound No. 11) | 350 | 440 | 0.63 | 0.32 | 0.26 | 2.0 | 3.6 |
| 15e (Compound No. 12) | 350 | 440 | 0.95 | 0.44 | 0.17 | 2.2 | 4.5 |
| 15c (Compound No. 13) | 350 | 450 | 0.81 | 0.18 | 0.19 | 1.2 | 3.9 |
| 15d (Compound No. 14) | 380 | 540 | 1.33 | 1.25 | 1.05 | 1.1 | 1.3 |
| 16c (Compound No. 15) | 430 | 620 | 1.71 | 1.43 | 1.29 | 1.2 | 1.7 |
| 16d (Compound No. 16) | 405 | 630 | 3.82 | 1.10 | 1.26 | 3.5 | 3.9 |
| 16b (Compound No. 17) | 430 | 630 | 9.22 | 9.45 | 56.71 | 1.0 | 2.1 |
| 16e (Compound No. 18) | 405 | 610 | 3.90 | 1.55 | 1.59 | 2.5 | 3.0 |

$^a$Fold increase (FI) = fluorescence intensity of probe bound to tau aggregate (or Aβ aggregate or BSA)/fluorescence intensity of probe (free)
$^b$Selectivity index (SI) = fluorescence intensity of probe bound to Tau aggregate/fluorescence intensity of probe bound to Aβ aggregate (or BSA)

Industrial Availability

The novel quinoline derivative compounds of the present invention exhibit spontaneously near-infrared fluorescence, and selectively bind to tau fiber proteins and thus exhibit a strong effect of detecting tau fiber proteins. Thus, the compound can be usefully used as a near-infrared fluorescent probe composition for detecting tau fiber proteins for early diagnosis of tauopathy caused by tau aggregates, such as Alzheimer's disease and Parkinson's disease, and thus has industrial applicability.

The novel quinoline derivative compound according to the present invention can specifically bind to tau fiber protein aggregates, thereby specifically diagnosing conditions and disorders associated with tau fiber protein aggregates through fluorescence changes.

The novel compound according to the present invention is a phosphor organic low-molecular-weight tracer compound that selectively binds to tau fiber protein aggregates and can be useful for early diagnosis of tauopathy including Alzheimer's disease, dementia, Parkinson's disease, progressive nuclear paralysis, corticobasal degeneration, argyrophilic grain disease, Pick's disease, frontotemporal dementia and the like, that is, brain nervous system diseases caused by entanglement of tau fiber proteins.

The novel compound according to the present invention can contribute to the improvement of bio-imaging methods through early diagnosis of tauopathy using a noninvasive method, and can easily analyze the degree of progression of pathology associated with tau fiber protein aggregation by fluorescently imaging and quantifying tau fiber proteins.

The invention has been described in detail with reference to preferred embodiments thereof. However, it will be appreciated by those skilled in the art that changes may be made in these embodiments without departing from the principles and spirit of the invention, the scope of which is defined in the appended claims and their equivalents.

What is claimed is:

1. A quinoline derivative compound, wherein the compound is any one selected from the group consisting of the following compounds:
   Compound No. 2 (E)-1-(4-(tert-butoxycarboxamino)phenyl)-3-(6-methoxyquinolin-2-yl)prop-2-en-1-one;
   Compound No. 3 (E)-1-(4-aminophenyl)-3-(6-hydroxyquinolin-2-yl)prop-2-en-1-one;
   Compound No. 5 (E)-1-(4-bromophenyl)-3-(6-methoxyquinolin-2-yl)prop-2-en-1-one;
   Compound No. 6 (E)-6-methoxy-2-(4-(trifluoromethyl)styryl)quinolone;
   Compound No. 8 6-methoxy-2-((/E,3E)-4-(3-chlorophenyl)buta-1,3-dien-1-yl)quinolone;
   Compound No. 9 6-methoxy-2-((/E,3E)-4-(3-nitrophenyl)buta-1,3-dien-1-yl)quinolone;
   Compound No. 10 6-methoxy-2-((/E,3E)-4-(2,4-difluorophenyl)buta-1,3-dien-1-yl)quinolone;
   Compound No. 11 4-((1E,3E)-4-(6-methoxyquinolin-2-yl)buta-1,3-diene-1-yl)-N-methylanaline;
   Compound No. 13 4-((1E,3E)-4-(6-methoxyquinolin-2-yl)buta-1,3-diene-1-yl)-N,N-dimethylaniline;
   Compound No. 15 (2E,4E)-5-(4-(dimethylamino)phenyl)-1-(6-methoxyquinolin-2-yl)penta-2,4-dien-1-one;
   Compound No. 16 (2E,4E)-5-(6-(dimethylamino)pyridin-3-yl)-1-(6-methoxyquinolin-2-yl)penta-2,4-diene-1-one;
   Compound No. 17 (2E,4E)-1-(6-methoxyquinolin-2-yl)-5-(4-(methylamino)phenyl)penta-2,4-dien-1-one; and
   Compound No. 18 (2E,4E)-5-(44(2-hydroxyethyl)(methyl)amino)phenyl)-1-(6-methoxyquinolin-2-yl)penta-2,4-dien-1-one.

2. A method for diagnosing a subject having a tau fiber protein, wherein the method comprises detecting a tau aggregate in cells or tissues using one or more compounds selected from the group consisting of the following compounds, as near-infrared fluorescent (NIRF) probe:

Compound No. 2 (E)-1-(4-(tert-butoxycarboxamino)phenyl)-3-(6-methoxyquinolin-2-yl)prop-2-en-1-one;

Compound No. 3 (E)-1-(4-aminophenyl)-3-(6-hydroxyquinolin-2-yl)prop-2-en-1-one;

Compound No. 5 (E)-1-(4-bromophenyl)-3-(6-methoxyquinolin-2-yl)prop-2-en-1-one;

Compound No. 6 (E)-6-methoxy-2-(4-(trifluoromethyl)styryl)quinolone;

Compound No. 8 6-methoxy-2-((/E,3E)-4-(3-chlorophenyl)buta-1,3-dien-1-yl)quinolone;

Compound No. 9 6-methoxy-2-((/E,3E)-4-(3-nitrophenyl)buta-1,3-dien-1-yl)quinolone;

Compound No. 10 6-methoxy-2-((/E,3E)-4-(2,4-difluorophenyl)buta-1,3-dien-1-yl)quinolone;

Compound No. 11 4-((1E,3E)-4-(6-methoxyquinolin-2-yl)buta-1,3-diene-1-yl)-N-methylanaline;

Compound No. 13 4-((1E,3E)-4-(6-methoxyquinolin-2-yl)buta-1,3-diene-1-yl)-N,N-dimethylaniline;

Compound No. 15 (2E,4E)-5-(4-(dimethylamino)phenyl)-1-(6-methoxyquinolin-2-yl)penta-2,4-dien-1-one;

Compound No. 16 (2E,4E)-5-(6-(dimethylamino)pyridin-3-yl)-1-(6-methoxyquinolin-2-yl)penta-2,4-diene-1-one;

Compound No. 17 (2E,4E)-1-(6-methoxyquinolin-2-yl)-5-(4-(methylamino)phenyl)penta-2,4-dien-1-one; and Compound No. 18 (2E,4E)-5-(44(2-hydroxyethyl)(methyl)amino)phenyl)-1-(6-methoxyquinolin-2-yl)penta-2,4-dien-1-one.

3. The method according to claim 2, wherein the subject having a tau fiber protein has tauopathy.

4. The method according to claim 3, wherein the tauopathy is any one selected from the group consisting of Alzheimer's disease, Parkinson's disease, progressive nuclear paralysis, corticobasal degeneration, argyrophilic grain disease, Pick's disease and frontotemporal dementia.

5. The method according to claim 2, wherein the detecting is conducted in vitro or ex vivo.

* * * * *